United States Patent [19]

Wilson et al.

[11] 4,310,440

[45] Jan. 12, 1982

[54] CRYSTALLINE METALLOPHOSPHATE COMPOSITIONS

[75] Inventors: Stephen T. Wilson, Shrub Oak; Brent M. Lok, New York; Edith M. Flanigen, White Plains, all of N.Y.

[73] Assignee: Union Carbide Corporation, New York, N.Y.

[21] Appl. No.: 166,333

[22] Filed: Jul. 7, 1980

[51] Int. Cl.$^3$ .................. B01J 27/14; B01J 31/02; C01B 15/16

[52] U.S. Cl. .................. 252/435; 252/430; 423/305

[58] Field of Search ............. 252/435, 430; 423/305

[56] References Cited

U.S. PATENT DOCUMENTS

| | | | |
|---|---|---|---|
| 2,282,602 | 5/1942 | Drennan | 252/435 X |
| 2,330,115 | 9/1943 | Drennan | 252/435 X |
| 3,941,871 | 3/1976 | Dwyer et al. | 423/326 |
| 3,969,273 | 7/1976 | Brown et al. | 252/435 |
| 4,061,724 | 12/1977 | Grose et al. | 423/335 |
| 4,066,572 | 1/1978 | Choca | 252/435 X |
| 4,132,669 | 1/1979 | Choca et al. | 252/435 |

OTHER PUBLICATIONS

Bull. Soc. Chim., France, 1961, F. D'Yvoire.

Primary Examiner—Andrew Metz
Assistant Examiner—William G. Wright
Attorney, Agent, or Firm—Richard G. Miller

[57] ABSTRACT

A novel family of crystalline, microporous aluminophosphate compositions is synthesized by hydrothermal crystallization at elevated temperatures of aluminophosphate gels containing a molecular structure-forming template. The family comprises a number of distinct species, each with a unique crystal structure. Calcination removes volatile extraneous matter from the intracrystalline void space and yields microporous crystalline adsorbents with uniform pores, the dimensions of which vary, among the individual species, from about 3A to 10A in diameter. The compositions represent a new class of adsorbents of the molecular sieve type, and also exhibit properties somewhat analogous to zeolitic molecular sieves which render them useful as catalysts or catalyst bases in chemical reactions such as hydrocarbon conversions.

26 Claims, No Drawings

CRYSTALLINE METALLOPHOSPHATE COMPOSITIONS

The present invention relates in general to a novel family of crystalline compositions and to the method for their synthesis. More particularly it relates to crystalline microporous aluminophosphate compositions and to hydrothermal processes for preparing same.

Molecular sieves of the crystalline zeolite type are well known in the art and now comprise over 150 species of both naturally occurring and synthetic compositions. In general the crystalline zeolites are aluminosilicates whose frameworks are formed from $AlO_4$- and $SiO_4$ tetrahedra joined by the sharing of oxygen atoms and characterized by having pore openings of uniform dimensions, having a significant ion-exchange capacity and being capable of reversibly desorbing an adsorbed phase which is dispersed through the internal voids of the crystal without displacing any atoms which make up the permanent crystal structure.

Other crystalline microporous phases which are not zeolitic, i.e. do not contain $AlO_4$-tetrahedra as essential framework constituents, but which exhibit the ion exchange and/or adsorption characteristics of the zeolitic phases are also known. Metallorganosilicates which are said to possess ion-exchange properties, have uniform pores and are capable of reversibly adsorbing molecules having molecular diameters of about 6A or less are reported in U.S. Pat. No. 3,941,871 issued Mar. 2, 1976 to Dwyer et al. Also a pure silica polymorph having molecular sieving properties and a neutral framework containing no cations or cation sites is defined in U.S. Pat. No. 4,061,724 issued Dec. 6, 1977 to R. W. Grose et al.

We have now discovered a new class of molecular sieve materials which are microporous three-dimensional crystalline aluminophosphate phases having uniform pore dimensions ranging from about 3A to about 10A and capable of making size selective separations of molecular species.

The chemistry of aluminum phosphates has been reviewed by J. H. Morris et al. (Chem. Soc. Rev., 6, 173 (1977)). The phosphates with an $Al_2O_3:P_2O_5$ molar ratio of 1:1 are the most common, and have been the most widely studied. Anhydrous $AlPO_4$ is isoelectronic and isostructural with silica and exists in quartz (as berlinite), tridymite, and cristobalite forms possessing frameworks of alternating $AlO_4$ and $PO_4$ tetrahedra. In addition to these, F. D'Yvoire [Bull. Soc. Chem. France, 1762 (1961)] has described five anhydrous crystalline $AlPO_4$ forms which have no silica analogs.

Two hydrates of $AlPO_4$ with the stoichiometry $AlPO_4 \cdot 2H_2O$, metavariscite and variscite, occur in natural and synthetic forms. Their structures were determined by Kniep and coworkers (Acta Crysta., B29, 2292 (1973); ibid., B33 263 (1977), and both can be described as frameworks of alternating octahedral $AlO_4(H_2O)_2$ and tetrahedral $PO_4$ units. In both the metavariscite and variscite structures the $H_2O$ is chemically bound to the Al and, although small amounts of this water can be removed reversibly, complete dehydration is irreversible and leads to significant structural changes and the formation of anhydrous $AlPO_4$ phases.

In addition to these, six crystallographically unique, metastable hydrates have been synthesized by F. D'Yvoire (ibid.). Of these, four are reported to be reversibly dehydrated under mild conditions to yield anhydrous phases, but in each case significant changes in framework topology occurred. These changes were reported to be reversible by rehydration. It is possible therefore that the interaction between water and these aluminophosphate phases results in chemical bonding, such as the formation of $AlO_4(H_2O)_2$ octahedra, rather than physisorption.

The hydrothermal synthesis of aluminosphates in the presence of various alkali metal, alkaline earth, and $NH_4$ cations has been reported by Haseman and coworkers (Soil Sci. Soc. Proceed., 76 (1950); Soil Sci., 70, 257-271 (1950)), by Cole and Jackson (J. Phys. Chem.), 54, 128-142 (1950)), and by Golub and Boldog (Russ. Jour. Inorg. Chem., 21, 45 (1976)). A variety of known minerals (e.g. palmierite, taranakite, wavellite, variscite) and many novel crystalline materials were obtained. Virtually all of these materials had Al/P ratios different from 1.0. Although most of the products had appreciable $H_2O$ content only one product was examined by X-ray powder diffraction after dehydration. This product, taranakite, became amorphous at 125° C. The stability of the other phases is unknown.

R. M. Barrer and D. J. Marshall (J. Chem. Soc., 6616 (1965)) attempted to substitute P for Si during hydrothermal crystallization of mixed frameworks analogous to aluminosilicates. The crystalline products obtained from synthesis mixtures containing sources of Al, Si, and P were predominately aluminosilicates (e.g. montmorillonite, analcite, and cancrinite) and phosphates (e.g. hydroxyapatite). Several unidentified crystalline solids were observed, characterized solely by their X-ray powder diffraction patterns. Evidence for phosphorus incorporation in the aluminosilicate structures or silicon incorporation in the hydroxyapatites was not obtained, however.

G. Kuehl has used phosphate as a complexing ion for aluminum in the hydrothermal synthesis of certain zeolites (Proceedings of the London Conf. on Molecular Sieves, April 1967, p. 85; Inorg. Chem., 10, 2488 (1971)). Presumably the phosphate complexes some of the aluminum, lowering the effective concentration of the more reactive hydroxoaluminate species in the reaction mixture and, thereby, increases the ratio of silicate to hydroxoaluminate. The zeolite products had a higher Si/Al ratio than normal and presumably no incorporation of P into the zeolite frameworks was observed. In one case, a high-silica form of zeolite A contained phosphate intercalated in the sodalite cages.

In an attempt to isolate the aluminophosphate species formed when phosphate is added to a zeolite synthesis mixture, G. Kuehl prepared the crystalline compounds $[(CH_3)_4N]_3[Al(PO_4)_2] \cdot X H_2O$ where $X=10, 4,$ and $1.5$. They were characterized by X-ray powder diffraction, thermal, and elemental analysis, and were described as salts containing isolated $Al(PO_4)_2(OH_2)_x{}^{3-}$ units. Removal of all the $H_2O$ caused the decomposition of these compounds (U.S. Pat. No. 3,386,801 (1968); J. Inorg. Nucl. Chem., 31, 1943 (1969)).

The novel generic class of aluminophosphates of the present invention have an essential crystalline framework structure whose chemical composition expressed in terms of molar ratios of oxides, is $Al_2O_3 : 1.0 \pm 0.2\ P_2O_5;$ said framework structure being microporous in which the pores are uniform and in each species have nominal diameters within the range of from 3 to 10 Angstroms; an intracrystalline adsorption capacity for water at 4.6 torr and 24° C. of at least 3.5 weight percent; the adsorption of water being completely reversible while retaining the same essential framework topology in both the hydrated and dehydrated state. By the term "essential framework topology" is meant the spatial arrangement of the primary Al-O and P-O bond linkages. No change in the framework topology indicates that there is no disruption of these primary bond linkages.

The present aluminophosphates are prepared by hydrothermal crystallization of a reaction mixture prepared by combining a reactive source of phosphate, alumina and water and at least one structure-directing or templating agent which can include an organic amine and a quaternary ammonium salt. In the as-synthesized form the structure-directing agent is contained within the framework structure of the aluminophosphate in amounts which vary from species to species but usually does not exceed one pole per mole of $Al_2O_3$ thereof. This structure-directing agent is readily removed by water washing or calcination and does not appear to be an essential constituent of the product aluminophosphate as evidenced by essentially complete absence of ion-exchangeability of the as-synthesized compositions and also the absence of any internally-contained organic molecules in the as-synthesized form of at least one species of the generic class. Evidence that a structure-directing agent is a critical constituent is contained in certain of the illustrative examples appearing hereinafter, wherein reaction mixtures otherwise identical to those which yield products of the present invention except for the presence of templating agents, yield instead the previously known aluminophosphate phases $AlPO_4.1.1-1.3$ $H_2O$, $AlPO_4$-tridymite, $AlPO_4$-quartz and $AlPO_4$-cristobalite.

Broadly the preparative process comprises forming a reaction mixture which in terms of molar ratios of oxides is $Al_2O_3:1\pm0.5P_2O_5:7-100H_2O$ and containing from about 0.2 to 2.0 moles of templating agent per mole of $Al_2O_3$. The reaction mixture is placed in a reaction vessel inert toward the reaction system and heated at a temperature of at least about 100° C., preferably between 100° C. and 300° C., until crystallized, usually a period from 2 hours to 2 weeks. The solid crystalline reaction product is then recovered by any convenient method, such as filtration or centrifugation, washed with water and dried at a temperature between ambient and 110° C. in air.

In a preferred crystallization method the source of phosphate is phosphoric acid, and source of alumina is a pseudo-boehmite hydrated aluminum oxide, the temperature is 125° C. to 200° C., and the crystallization time is from one to seven days. The preferred ratio of oxides in the reaction mixture is $Al_2O_3:0.8-1.2$ $P_2O_5:25-75$ $H_2O$ In general the most preferred reaction mixture contains per mole of $Al_2O_3$ from about 0.5–1.5 moles of templating agent, from 40–50 moles of water and about 1.0 mole of $P_2O_5$.

Not all templating agents suitably employed in the preparation of certain species of aluminophosphates of this invention are suitable for the preparation of all members of the generic class. The relationship of specific templating agents to the individual product species is apparent from the illustrative Examples set forth hereinafter.

The method of preparation and the physical and chemical properties of the various members of the present class of novel aluminophosphates are illustrated and characterized, respectively, in the following examples. The species compounds are denominated as $AlPO_4$-n wherein "n" is a number specific to each individual member.

EXAMPLE 1 Preparation of $AlPO_4$-5

A reaction mixture was prepared by combining 46.1 grams of 85% orthophsophoric acid ($H_3PO_4$) and 100.0 grams of water, to which was added 27.5 grams of a hydrated aluminum oxide (a pseudo-boehmite phase, 74.2 wt% $Al_2O_3$, 25.8 wt.% $H_2O$, a commercial product available under the trademark CATAPAL SB of the Conoco Chemicals Division of Continental Oil Company, U.S.A.) and stirred until homogeneous. To this mixture was added 176.8 grams of an aqueous solution of 23 wt.% tetrapropylammonium hydroxide (TPAOH), and the mixture stirred until homogeneous. The composition of the final reaction mixture in molar oxide ratios was:

0.5 $(TPA)_2O:Al_2O_3:P_2O_5:73H_2O$

The reaction mixture was sealed in a stainless steel pressure vessel lined with polytetrafluoroethylene and heated in an oven at 150° C. at autogenous pressure for 43 hours. The solid reaction product was recovered by filtration, washed with water, and dried in air at room temperature. The major phase in the product had an X-ray powder diffraction pattern characterized by the following data wherein "I" is the intensity and "d" the interplanar spacing. The product also contained a minor amount of another crystalline impurity.

| $2\theta$ | d | $100 \times I/I_o$ |
|---|---|---|
| 7.50 | 11.8 | 100 |
| 12.95 | 6.84 | 11 |
| 14.95 | 5.93 | 28 |
| 19.75 | 4.50 | 66 |
| 20.95 | 4.24 | 63 |
| 22.4 | 3.97 | 94 |
| 24.65 | 3.61 | 5 |
| 26.00 | 3.43 | 37 |
| 28.95 | 3.08 | 21 |
| 30.05 | 2.97 | 22 |
| 33.50 | 2.67 | 5 |
| 34.50 | 2.60 | 19 |
| 36.95 | 2.43 | 5 |
| 37.50 | 2.40 | 13 |
| 40.75 | 2.21 | 1 |
| 41.60 | 2.17 | 4 |
| 42.45 | 2.13 | 4 |
| 43.65 | 2.07 | 3 |
| 44.95 | 2.02 | 2 |
| 47.70 | 1.91 | 6 |

This X-ray pattern and all other X-ray patterns appearing hereinafter were obtained using standard X-ray powder diffraction techniques. The radiation source was a high-intensity, copper target, X-ray tube operated at 50 Kv and 40 ma. The diffraction pattern from the copper $K\alpha$ radiation and graphite monochromator is suitably recorded by an X-ray spectrometer scintillation counter, pulse height analyzer and strip chart recorder. Flat compressed powder samples are scanned at 2° (2 theta) per minute, using a two second time constant. Interplanar spacings (d) are obtained from the position of the diffraction peaks expressed as $2\theta$ where $\theta$ is the Bragg angle as observed on the strip chart. Intensities are determined from the heights of diffraction peaks after subtracting background.

EXAMPLE 2 Preparation of AlPO$_4$-5

(a) A reaction mixture was prepared by combining 23.1 grams of 85% orthophosphoric acid (H$_3$PO$_4$) and 44.0 grams of water, to which was added 13.7 grams of the same hydrated aluminum oxide employed in Example 1, and stirred until homogeneous. To this mixture was added 35.1 grams of an aqueous solution of 58 wt.% tetrapropylammonium hydroxide (TPAOH), and the mixture stirred until homogeneous. The composition of the final reaction mixture in molar oxide ratios was:

0.5 (TPA)$_2$O:Al$_2$O$_3$:P$_2$O$_5$:40H$_2$O

The reaction mixture was sealed in a stainless steel pressure vessel lined with polytetrafluoroethylene and heated in an oven at 150° C. at autogenous pressure for 65 hours. The solid reaction product was recovered by filtration, washed with water, and dried in air at room temperature. A portion of the solids was submitted for X-ray analysis and chemical analysis.

Chemical analysis showed 7.5 wt.% C, 0.67 wt.% N, 34.2 wt.% Al$_2$O$_3$, 46.5 wt.% P$_2$O$_5$, 17.7 wt.% LOI (Loss on Ignition at 1000° C. for 4 hr) giving a product composition in molar oxide ratios of:

0.08 (TPA)$_2$O:1.00Al$_2$O$_3$:0.98P$_2$O$_5$:1.3H$_2$O

The above product had an X-ray powder diffraction pattern essentially identical to that of the major phase in Example 1, and contained no crystalline impurities. This product was designated AlPO$_4$-5.

(b) A portion of the solid crystalline product obtained from a similar procedure as in part (a) above and exhibiting an X-ray powder diffraction pattern essentially identical to that in Example 1 was calcined in air at about 500° C. for 2 hours. The calcined product had an X-ray powder diffraction pattern essentially identical to that in Example 1.

EXAMPLE 3 Preparation of AlPO$_4$-5

(a) A reaction mixture was prepared by combining 46.1 grams of 85% orthophosphoric acid (H$_3$PO$_4$) and 118.6 grams of water, to which was added 27.5 grams of a pseudo-boehmite phase (74.2 wt.% Al$_2$O$_3$, 25.8 wt.% H$_2$O), and stirred until homogeneous. To this mixture was added 29.2 grams of tripropylamine (Pr$_3$N) and the mixture stirred until homogeneous. The composition of the final reaction mixture in molar oxide ratios was:

1.0 Pr$_3$N:Al$_2$O$_3$:P$_2$O$_5$:40H$_2$O

The reaction mixture was sealed in a stainless steel pressure vessel lined with polytetrafluoroethylene and heated in an oven at 150° C. at autogenous pressure for 70 hours. The solid reaction product was recovered by filtration, washed with water, and dried in air at room temperature. Chemical analysis showed 5.7 wt.% C, 0.72 wt.% N, 34.0 wt.% Al$_2$O$_3$, 48.1 wt.% P$_2$O$_5$, 16.4 wt.% LOI, giving a product composition in molar oxide ratios of:

0.16 Pr$_3$N:1.00Al$_2$O$_3$:1.02 P$_2$O$_5$:1.5H$_2$O

The above product had an X-ray powder diffraction pattern virtually identical to that of the major phase set forth in Example 1 and contained no crystalline impurities.

(b) A portion of the solid crystalline product obtained above was calcined in air at about 600° C. for 2 hours. The calcined product had an X-ray powder diffraction pattern essentially the same as that of the as-synthesized product of part (a) above.

EXAMPLE 4 Preparation of AlPO$_4$-5

A reaction mixture was prepared by combining 23.1 grams of 85% orthophosphoric acid (H$_3$PO$_4$) and 59.6 grams of water, to which was added 13.7 grams of a hydrated aluminum oxide, (74.2 wt.% Al$_2$O$_3$, 25.8 wt.% H$_2$O), and stirred until homogeneous. To this mixture was added 8.6 grams of tripropylamine (Pr$_3$N) and the mixture stirred until homogeneous. The composition of the final reaction mixture in molar oxide ratios was:

0.6 Pr$_3$N:Al$_2$O$_3$:P$_2$O$_5$:40H$_2$O

The reaction mixture was sealed in a stainless steel pressure vessel lined with an inert plastic material and heated in an oven at 150° C. at autogenous pressure for 4 hours. The solid reaction product was recovered by filtration, washed with water, and dried in air at room temperature. The X-ray powder diffraction pattern of this product showed the crystalline AlPO$_3$-5 product of example 3 as the major phase, with a minor amount of a crystalline impurity being also present.

EXAMPLE 5 Preparation of AlPO$_4$-5

A reaction mixture was prepared by combining 46.1 grams of 85% orthophosphoric acid (H$_3$PO$_4$) and 119.2 grams of water, to which was added 27.5 grams of a hydrated aluminum oxide (74.2 wt.% Al$_2$O$_3$, 25.8 wt.% H$_2$O), and stirred until homogeneous. To this mixture was added 30.4 grams of triethylamine (Et$_3$N), and the mixture stirred until homogeneous. The composition of the final reaction mixture in molar oxide ratios was:

1.5 Et$_3$N:Al$_2$O$_3$:P$_2$O$_5$:40H$_2$O

The reaction mixture was sealed in a stainless steel pressure vessel lined with polytetrafluoroethylene and heated in an oven at 200° C. at autogenous pressure for 27 hours. The solid reaction product was recovered by filtration, washed with water, and dried in air at room temperature. Chemical analysis of the product indicated the presence of 4.8 wt.% C, 0.97 wt.% N, 35.3 wt.% Al$_2$O$_3$, 49.7 wt.% P$_2$O$_5$ and 13.6 wt.% LOI, giving a product composition in molar oxide ratios of:

0.19 Et$_3$N:1.00Al$_2$O$_3$:1.01 P$_2$O$_5$:1.1H$_2$O

The above product had an X-ray powder diffraction pattern essentially identical to that of the AlPO$_4$-5 product of example 1 and contained no crystalline impurities.

EXAMPLE 6 Preparation of AlPO$_4$-5

(a) A reaction mixture was prepared by combining 18.5 grams of 85% orthophosphoric acid (H$_3$PO$_4$) and 45.9 grams of water, to which was added 13.7 grams of a pseudo-boehmite phase (74.2 wt.% Al$_2$O$_3$, 25.8 wt.% H$_2$O), and stirred until homogeneous. To this mixture was added 25.9 grams of an aqueous solution of 57 wt.% tetrapropylammonium hydroxide (TPAOH), and the mixture in molar oxide ratios was:

0.5 (TPA)$_2$O:Al$_2$O$_3$:0.8 P$_2$O$_5$:40H$_2$O

The reaction mixture was placed in a stainless steel pressure vessel lined with an inert plastic material and heated in an oven at 150° C. at autogenous pressure for 72 hours. The solid reaction product was recovered by repeated centrifugation and washing with water, followed by filtration, washing, and drying in air at room temperature. The X-ray powder diffraction pattern of the dried product showed the major phase to be identical to AlPO$_4$-5 of example 1.

(b) A reaction mixture free of a structure-directing agent was prepared by combining 46.1 grams of 85% orthophosphoric acid (H$_3$PO$_4$) and 120 grams of water, to which was added 27.5 grams of the same hydrated aluminum oxide as in part (a) above, and stirred until homogeneous. The composition of the final reaction mixture in molar oxide ratios was:

$Al_2O_3:P_2O_5:40H_2O$

The reaction mixture was sealed in a stainless steel pressure vessel lined with polytetrafluoroethylene and heated in an oven at 150° C. at autogenous pressure for 72 hours. The solid reaction product was recovered by filtration, washed with water, and dried in air at 110° C. The resulting product had an X-ray powder diffraction pattern indicating a mixture of known $AlPO_4$ phases: $AlPO_41.1-1.3H_2O$, and two structural analogs of crystalline silica, namely $AlPO_4$ (quartz) and $AlPO_4$ (tridymite). An identical reaction mixture heated at 200° for 24 hours produced a mixture of the same known $AlPO_4$ phases, the major products being $AlPO_4$ (quartz) and $AlPO_4$ (tridymite). No microporous $AlPO_4$ phases of the present invention were observed.

EXAMPLE 7 Preparation of $AlPO_4$-5

A reaction mixture was prepared by combining 37.8 grams of 85% orthophosphoric acid ($H_3PO_4$) and 177 grams of water, to which was added 67 grams of aluminum isopropoxide and stirred until homogeneous. The mixture was filtered and washed with water. To this mixture was added 145 grams of an aqueous solution of 23 wt.% tetrapropylammonium hydroxide (TPAOH), and the mixture stirred until homogeneous. The composition of the final reaction mixture in molar oxide ratios was:

$0.5 \ (TPA)_2O:Al_2O_3:P_2O_5:xH_2O$

The reaction mixture was placed in a stainless steel pressure vessel lined with polytetrafluoroethylene and heated in an oven at 150° C. at autogenous pressure for 276 hours. The solid reaction product was recovered by filtration, washed with water, and dried in air at 110° C. The dried product was $AlPO_4$-5 as indicated by an X-ray powder diffraction pattern which was essentially the same as the $AlPO_4$-5 in example 1.

EXAMPLES 8–26 Preparation of $AlPO_4$-5

A procedure similar to that in example 3 was followed except where indicated in Table A below. The composition of each final mixture in molar oxide ratios was:

$1.0 \ R:Al_2O_3:P_2O_5:40H_2O$ except where noted in Table A. A portion of the solid product from each reaction was examined by X-ray analysis and in each case a phase characterized by an X-ray powder diffraction pattern essentially the same as the $AlPO_4$-5 phase in example 1 was observed alone or in admixture with other products.

TABLE A

| EX. # | R | REACTION TIME (Hrs.) | REACTION TEMP., (°C.) |
|---|---|---|---|
| 8 | $(C_2H_5)_4NOH$(tetraethylammonium hydroxide) | 24 | 200 |
| 9 | $N(CH_2CH_2OH)_3$ (triethanolamine) | 72 | 150 |
| 10 | piperidine | 24 | 150 |
| 11 | 2-methylpyridine | 168 | 150 |
| 12 | cyclohexylamine | 168 | 150 |
| 13 | N,N-dimethylbenzylamine | 168 | 150 |
| 14 | N,N-diethylethanolamine | 24 | 200 |
| 15 | dicyclohexylamine | 24 | 150 |
| 16 | N-N-dimethylethanolamine | 24 | 150 |
| 17 | $[(CH_3)_3NCH_2CH_2OH)OH^1$ | 52 | 150 |
| 18 | N,N-dimethylpiperazine[1] | 24 | 200 |
| 19 | 1,4-diazabicyclo (2,2,2) octane DABCO[2] | 192 | 200 |
| 20 | N-methyl-diethanolamine[1] | 24 | 200 |
| 21 | N-methyl-ethanolamine[1] | 24 | 200 |
| 22 | N-methylpiperidine | 24 | 200 |
| 23 | 3-methylpiperidine | 168 | 150 |
| 24 | N-methylcyclohexylamine | 24 | 200 |
| 25 | 3-methylpyridine | 24 | 150 |
| 26 | 4-methylpyridine | 168 | 150 |

[1]The final reaction mixture contains 50 $H_2O$.
[2]The final reaction mixture contains 0.5 DABCO.

The species $AlPO_4$-5 as herein referred to is a crystalline metallophosphate whose essential framework structure has a chemical composition, expressed in terms of molar ratios of oxides, is $Al_2O_3:1.0\pm0.2 \ P_2O_5$ and having a characteristic X-ray powder diffraction pattern which contains at least the d-spacings set forth in Table 2, below:

TABLE 2

| 2θ | d | 100 × I/Io |
|---|---|---|
| 7.4–7.6 | 11.9–11.6 | 100 |
| 14.8–15.3 | 5.97–5.83 | 13–43 |
| 19.7–20.1 | 4.51–4.42 | 39–92 |
| 20.8–21.2 | 4.27–4.19 | 37–87 |
| 22.3–22.7 | 3.99–3.93 | 62–118 |
| 25.9–26.3 | 3.44–3.39 | 22–35 |

All of the $AlPO_4$-5 compositions for which the X-ray powder diffraction data has presently been obtained have patterns that are within the generalized pattern of Table 3, below:

TABLE 3

| 2θ | d | 100 × I/Io |
|---|---|---|
| 7.4–7.6 | 11.9–11.6 | 100 |
| 12.9–13.15 | 6.86–6.73 | 9–12 |
| 14.85–15.2 | 5.97–5.83 | 13–43 |
| 19.7–20.1 | 4.51–4.42 | 39–92 |
| 20.8–21.2 | 4.27–4.19 | 37–87 |
| 22.3–22.7 | 3.99–3.92 | 62–118 |
| 24.55–24.9 | 3.63–3.58 | 4–8 |
| 25.9–26.25 | 3.44–3.39 | 22–32 |
| 28.9–29.2 | 3.09–3.06 | 11–18 |
| 30.0–30.4 | 2.98–2.94 | 12–23 |
| 33.5–33.85 | 2.67–2.65 | 4–9 |
| 34.5–35.1 | 2.60–2.56 | 11–17 |
| 36.9–37.2 | 2.44–2.42 | 3–5 |
| 37.5–37.8 | 2.40–2.38 | 7–16 |
| 40.8–40.85 | 2.21–2.21 | 0–1 |
| 41.5–42.0 | 2.18–2.15 | 2–3 |
| 42.25–42.5 | 2.14–2.13 | 0–4 |
| 42.7–42.8 | 2.12–2.11 | 0–3 |
| 43.6–44.0 | 2.08–2.06 | 0–2 |
| 45.0–45.4 | 2.01–2.00 | 0–2 |
| 46.2 | 1.96 | 0–1 |
| 47.8 | 1.90 | 0–4 |
| 48.0–48.4 | 1.90–1.87 | 0–5 |
| 51.5–51.6 | 1.77–1.77 | 0–2 |
| 52.0 | 1.76 | 0–2 |
| 55.8–56.0 | 1.65–1.64 | 0–2 |

EXAMPLE 27 Preparation of AlPO$_4$-8

(a) A reaction mixture was prepared by combining 8.9 grams of 85% orthophosphoric acid (H$_3$PO$_4$) and 6 grams of water, to which was added 5.3 grams of a hydrated aluminum oxide (a pseudo-boehmite phase, 74.2 wt.% Al$_2$O$_3$, 25.8 wt.% H$_2$O); and 6.0 grams of water, and stirred until homogeneous. To this mixture was added 27.2 grams of an aqueous solution of 37 wt.% tetrabutylammonium hydroxide (TBAOH), and 2.0 grams of water and the mixture stirred until homogeneous. The composition of the final reaction mixture in molar oxide ratio was:

0.5 (TBA)$_2$O:Al$_2$O$_3$:P$_2$O$_5$:52H$_2$O

The reaction mixture was sealed in a stainless steel pressure vessel lined with an inert plastic material and heated in an oven at 150° C. at autogenous pressure for 145 hours. The solid reaction product was recovered by filtration, washed with water, and dried in air at 115° C. Chemical analysis showed the product to contain 0.2 wt.% C, <0.05 wt.% N, 34.7 wt.% Al$_2$O$_3$, 46.6 wt.% P$_2$O$_5$, 18.4 wt.% LOI, giving a product composition in molar oxide ratios of:

1.00 Al$_2$O$_3$:0.97 P$_2$O$_5$:3.00H$_2$O

The major phase in the above product had an X-ray powder diffraction pattern characterized by the following data wherein "I" is the intensity and "d" the interplanar spacing; the product also contained a minor amount of a crystalline impurity.

| 2θ | d | 100 × I/Io |
|---|---|---|
| 5.3 | 16.7 | 80 |
| 6.5 | 13.6 | 100 |
| 10.0 | 8.84 | 17 |
| 10.8 | 8.19 | 2 |
| 14.6 | 6.07 | 4 |
| 16.1 | 5.56 | 16 |
| 18.8 | 4.72 | 2 |
| 19.8 | 4.48 | 8 |
| 20.2 | 4.40 | 12 |
| 21.25 | 4.19 | 82 |
| 21.9 | 4.06 | 18 |
| 22.4 | 3.97 | 39 |
| 22.7 | 3.92 | (sh)* |
| 23.55 | 3.77 | 3 |
| 24.15 | 3.68 | 11 |
| 24.9 | 3.58 | 11 |
| 27.1 | 3.29 | 2 |
| 28.2 | 3.16 | 5 |
| 31.35 | 2.853 | 4 |
| 32.9 | 2.722 | 3 |
| 34.2 | 2.622 | 1 |
| 35.6 | 2.522 | 3 |
| 38.0 | 2.368 | 9 |
| 38.4 | 2.344 | 3 (sh)* |
| 43.2 | 2.094 | 2 |
| 46.9 | 1.937 | 1 |
| 49.5 | 1.841 | 3 |

*sh = shoulder

This product was designated AlPO$_4$-8. It is to be noted that only trace amounts of the tetrabutylammonium templating compound were present in the reaction product solids. This may indicate that a templating mechanism different from that in most other species of this invention is involved.

(b) A portion of the solid crystalline product obtained above was calcined in air at about 600° C. for 2 hours. The calcined product had an X-ray powder diffraction pattern essentially the same as that of the product of part (a) above.

EXAMPLES 28-30 Preparation of AlPO$_4$-8

A procedure similar to that in example 27 was followed except where indicated in Table B. The composition of each final reaction mixture in molar oxide ratios was:

1.0 R:Al$_2$O$_3$:P$_2$O$_5$:40H$_2$O where R is indicated in Table B. In each case a product phase characterized by an X-ray powder diffraction pattern essentially the same as that in example 27 was observed. Some extraneous phases were also present.

TABLE B

| EXAMPLE # | ORGANIC USED (R) | DIGESTION TIME (Hrs) | TEMP(°C.) |
|---|---|---|---|
| 28 | (n-C$_5$H$_{11}$)$_4$NOH | 24 | 150 |
| 29 | (n-C$_4$H$_9$)$_2$NH | 72 | 150 |
| 30 | (n-C$_5$H$_{11}$)$_2$NH* | 24 | 150 |

*Small amount of acetone used to wash solid product.

The species AlPO$_4$-8 as herein referred to is a crystalline metallophosphate whose essential framework structure has a chemical composition, expressed in terms of molar ratios of oxides, is Al$_2$O$_3$:1.0±0.2 P$_2$O$_5$ and having a characteristic X-ray powder diffraction pattern which contains at least the d-spacings set forth in TABLE 4 below:

TABLE 4

| 2θ | d | 100 × I/Io |
|---|---|---|
| 5.3–5.4 | 16.7–16.4 | 80–100 |
| 6.5–6.65 | 13.6–13.3 | 30–100 |
| 19.7–19.8 | 4.51–4.48 | 8–29 |
| 21.2–21.3 | 4.19–4.17 | 46–82 |
| 21.8–21.9 | 4.08–4.06 | 14–56 |
| 22.4–22.9 | 3.97–3.88 | 35–39 |

All of the AlPO$_4$-8 compositions for which the X-ray powder diffraction data has presently been obtained have patterns that are within the generalized pattern of TABLE 5 below:

TABLE 5

| 2θ | d | 100 × I/Io |
|---|---|---|
| 5.3–5.4 | 16.7–17.4 | 80–100 |
| 6.5–6.65 | 13.6–13.3 | 30–100 |
| 9.9–10.1 | 8.9–8.8 | 15–20 |
| 10.75–10.8 | 8.23–8.19 | 2–9 |
| 14.6–14.8 | 6.07–5.99 | 4–17 |
| 16.1–16.2 | 5.50–5.47 | 7–16 |
| 18.8–18.9 | 4.72–4.70 | 2–12 |
| 19.7–19.8 | 4.51–4.48 | 8–29 |
| 20.1–20.2 | 4.42–4.40 | 9–12 |
| 21.2–21.3 | 4.19–4.17 | 46–82 |
| 21.8–21.9 | 4.08–4.06 | 14–56 |
| 22.4–22.5 | 3.97–3.95 | 35–39 |
| 22.7–22.9 | 3.92–3.88 | |
| 23.55–23.65 | 3.77–3.76 | 3–7 |
| 24.1–24.2 | 3.69–3.68 | 9–11 |
| 24.9–25.1 | 3.58–3.55 | 11–15 |
| 27.1–27.2 | 3.29–3.28 | 2–16 |
| 28.2–28.3 | 3.16–3.15 | 4–8 |
| 31.35–31.4 | 2.853–2.849 | 4–6 |
| 32.9 | 2.722 | 3–8 |
| 34.2–34.3 | 2.622–2.614 | 1–2 |
| 35.6 | 2.522 | 0–3 |
| 38.0–38.2 | 2.368–2.356 | 9–16 |
| 38.4–38.6 | 2.344–2.332 | 3–18 |
| 43.2–43.3 | 2.094–2.090 | 2–4 |
| 46.9–47.0 | 1.937–1.933 | 1–2 |
| 49.4–49.5 | 1.845–1.841 | 2–4 |

EXAMPLE 31 Preparation of AlPO$_4$-9

(a) A reaction mixture was prepared by combining 27.6 grams of 85% orthophosphoric acid (H$_3$PO$_4$) and 36.0 grams of water, to which was added 16.5 grams of a hydrated aluminum oxide (a pseudo-boehmite phase, 74.2 wt.% Al$_2$O$_3$, 25.8 wt.% H$_2$O), and stirred until homogeneous. To this mixture was added 13.5 grams of 1,4-diazabicyclo (2.2.2)octane (DABCO) dissolved in 24.0 grams of water, then 11.7 grams of water, and the mixture stirred until homogeneous. The composition of the final reaction mixture in molar oxide ratios was:

1.0 DABCO:Al$_2$O$_3$:P$_2$O$_5$:40H$_2$O

The reaction mixture was sealed in a stainless steel pressure vessel lined with inert plastic and heated in an oven at 200° C. at autogenous pressure for 336 hours. The solid reaction product was recovered and washed by repeated centrifugation with water, and dried in air at 110° C. A portion of the solids was subjected to X-ray analysis and chemical analysis. Chemical analysis showed 10.6 wt.% C, 3.9 wt.%, N, 32.5 wt.% Al$_2$O$_3$, 46.5 wt.% P$_2$O$_5$, 19.0 wt.% LOI, giving a product composition in molar oxide ratios of:

0.46 DABCO:1.00 Al$_2$O$_3$:1.03 P$_2$O$_5$:0.44H$_2$O

The above product, denominated AlPO$_4$-9, had an X-ray powder diffraction pattern characterized by the following data, wherein "I" is the intensity and "d" the interplanar spacing:

| 2θ | d | 100 × I/Io |
|---|---|---|
| 8.4 | 10.5 | 12 |
| 11.1 | 7.97 | 43 |
| 12.5 | 7.08 | 18 |
| 14.0 | 6.33 | 6 |
| 15.1 | 5.87 | 5 |
| 16.8 | 5.28 | 11 |
| 18.3 | 4.85 | 29 |
| 19.3 | 4.60 | 11 |
| 21.0 | 4.23 | 100 |
| 21.9 | 4.06 | 30 |
| 22.3 | 3.99 | 18 |
| 22.8 | 3.90 | 30 |
| 25.4 | 3.51 | 38 |
| 25.7 | 3.47 | 79 |
| 26.5 | 3.36 | 13 |
| 27.7 | 3.22 | 21 |
| 28.5 | 3.13 | 29 |
| 30.6 | 2.92 | 5 |
| 31.45 | 2.843 | 10 |
| 31.8 | 2.814 | 27 |
| 32.4 | 2.763 | <1 |
| 33.15 | 2.702 | 12 |
| 33.7 | 2.660 | 18 |
| 34.3 | 2.614 | 5 |
| 34.8 | 2.578 | 3 |
| 35.5 | 2.529 | 4 |
| 36.4 | 2.468 | 1 |
| 37.8 | 2.380 | 4 |
| 38.35 | 2.347 | 10 |
| 38.45 | 2.341 | (sh)* |
| 38.9 | 2.315 | 10 |
| 41.3 | 2.186 | 2 |
| 42.15 | 2.144 | 6 |
| 42.6 | 2.122 | 4 |
| 44.55 | 2.034 | } 3 |
| 44.65 | 2.029 | |
| 46.5 | 1.953 | 2 |
| 48.0 | 1.895 | 3 |
| 48.4 | 1.881 | 1 |
| 49.75 | 1.833 | 7 |
| 50.2 | 1.817 | 9 |
| 51.0 | 1.791 | 1 |
| 51.7 | 1.768 | (sh)* } 11 |
| 51.9 | 1.762 | 11 |
| 53.65 | 1.708 | } 4 |
| 53.8 | 1.704 | |
| 55.35 | 1.660 | .7 |

(b) The procedure and gel composition of part (a) above were repeated except that the reaction mixture was heated for 168 hours. AlPO$_4$-9 was produced.

The species AlPO$_4$-9 as herein referred to is a crystalline metallophosphate whose essential framework structure has a chemical composition, expressed in terms of molar ratios of oxides, is Al$_2$O$_3$:1.0±0.2 P$_2$O$_5$ and having a characteristic X-ray powder diffraction pattern which contains at least the d-spacings set forth in TABLE 6 below:

TABLE 6

| 2θ | d | 100 × I/Io |
|---|---|---|
| 11.1–11.15 | 7.97–7.94 | 43–68 |
| 12.5–12.65 | 7.08–7.00 | 12–100 |
| 18.25–18.35 | 4.86–4.83 | 19–47 |
| 21.0–21.1 | 4.23–4.21 | 41–100 |
| 25.4–25.6 | 3.51–3.48 | 38–82 |
| 25.7–25.8 | 3.47–3.45 | 0–79 |

All of the AlPO$_4$-9 compositions for which the X-ray powder diffraction data has presently been obtained have patterns that are within the generalized pattern of TABLE 7 below:

TABLE 7

| 2θ | d | 100 × I/Io |
|---|---|---|
| 8.4–8.5 | 10.5–10.4 | <1–22 |
| 10.8 | 8.19 | (sh) |
| 11.1–11.15 | 7.97–7.94 | 43–68 |
| 12.5–12.65 | 7.08–7.00 | 12–100 |
| 14.0–14.2 | 6.33–6.24 | 2–8 |
| 15.1–15.25 | 5.87–5.81 | 4–6 |
| 16.8–16.85 | 5.28–5.26 | 3–13 |
| 18.25–18.35 | 4.86–4.83 | 19–47 |
| 19.3–19.5 | 4.60–4.55 | 2–15 |
| 21.0–21.1 | 4.23–4.21 | 41–100 |
| 21.9–22.05 | 4.06–4.03 | 11–39 |
| 22.2–22.3 | 4.00–3.99 | (sh)–20 |
| 22.7–22.8 | 3.92–3.90 | 30–39 |
| 25.4–25.6 | 3.51–3.48 | 38–82 |
| 25.7–25.8 | 3.47–3.45 | 0–79 |
| 26.5–26.7 | 3.36–3.34 | 13–16 |
| 27.7–27.9 | 3.22–3.20 | 4–21 |
| 28.2 | 3.16 | 0–(sh) |
| 28.45–28.55 | 3.136–3.126 | 16–36 |
| 30.3–30.7 | 2.950–2.912 | 5–21 |
| 31.45–31.6 | 2.844–2.831 | (sh) |
| 31.8–31.85 | 2.814–2.810 | 14–30 |
| 33.15–33.3 | 2.702–2.691 | 5–16 |
| 33.6–33.7 | 2.667–2.660 | 12–18 |
| 34.0 | 2.637 | 1–6 |
| 34.3–34.5 | 2.614–2.600 | 5–6 |
| 34.8–34.9 | 2.578–2.571 | 0–3 |
| 35.5–35.7 | 2.529–2.515 | 4–6 |
| 36.1–36.4 | 2.488–2.468 | 1–3 |
| 37.8–38.0 | 2.380–2.368 | 2–7 |
| 38.35–38.5 | 2.347–2.338 | 4–10 |
| 38.9–39.1 | 2.315–2.304 | 8–10 |
| 41.1–41.3 | 2.196–2.186 | 0–2 |
| 42.1–42.2 | 2.146–2.141 | 3–6 |
| 42.6–42.7 | 2.122–2.118 | 2–4 |
| 44.55–44.85 | 2.034–2.021 | 1–3 |
| 46.3–46.7 | 1.961–1.945 | 2–4 |
| 48.0–48.05 | 1.895–1.893 | 3–4 |
| 48.4–48.7 | 1.881–1.870 | <1–3 |
| 49.75–50.0 | 1.833–1.824 | 0–14 |
| 50.2–50.3 | 1.817–1.814 | 0–14 |

TABLE 7-continued

| 2θ | d | 100 × I/Io |
|---|---|---|
| 51.0–51.1 | 1.791–1.787 | <1–2 |
| 51.7–51.8 | 1.768–1.765 | (sh)–12 |
| 51.9–52.1 | 1.762–1.755 | 7–11 |
| 53.65–54.0 | 1.708–1.698 | 3–4 |
| 55.3–55.5 | 1.661–1.656 | 6–8 |

EXAMPLE 32 Preparation of AlPO$_4$-11

(a) A reaction mixture was prepared by combining 46.0 grams of 85% orthophosphoric acid (H$_3$PO$_4$) and 119.2 grams of water, to which was added 27.5 grams of the same hydrated aluminum oxide as in Example 1, and stirred until homogeneous. To this mixture was added 20.3 grams of di-(n-propyl)amine(Pr$_2$NH), and the mixture stirred until homogeneous. The composition of the final reaction mixture in molar oxide ratios was:

1.0 O Pr$_2$NH:Al$_2$O$_3$:P$_2$O$_5$:40H$_2$O

The reaction mixture was sealed in a stainless steel pressure vessel lined with polytetrafluoroethylene and heated in an oven at 200° C. at autogenous pressure for 24 hours. The solid reaction product was recovered by filtration, washed with water, and dried in air at room temperature. Chemical analysis of the reaction solids showed 5.1 wt.% C, 1.00 wt.% N, 37.6 wt.% Al$_2$O$_3$, 51.6 wt.% P$_2$O$_5$, 10.4 wt.% LOI, giving a product composition in molar oxide ratios of:

0.19 Pr$_2$NH:1.00 Al$_2$O$_3$:0.98 P$_2$O$_5$:0.48H$_2$O

The above product, denominated AlPO$_4$-11, had an X-ray powder diffraction pattern characterized by the following data, wherein "I" is the intensity and "d" the interplanar spacing:

| 2θ | d | 100 × I/Io |
|---|---|---|
| 8.15 | 10.85 | 34 |
| 9.5 | 9.31 | 49 |
| 13.3 | 6.66 | 16 |
| 15.7 | 5.64 | 30 |
| 16.35 | 5.42 | 5 |
| 19.0 | 4.67 | 6 |
| 20.55 | 4.32 | 50 |
| 21.0 | 4.23 | 100 |
| 22.2 | 4.00 | 58 |
| 22.65 | 3.93 | 75 |
| 23.25 | 3.83 | 67 |
| 24.6 | 3.62 | 10 |
| 24.8 | 3.59 | 11 |
| 26.4 | 3.38 | 13 |
| 26.7 | 3.34 | 17 |
| 28.5 (sh)* | 3.13 | 15 |
| 28.7 | 3.11 | |
| 29.2 | 3.06 | 6 |
| 29.6 | 3.02 | 9 |
| 31.5 | 2.84 | 10 |
| 33.0 | 2.71 | 15 |
| 34.3 | 2.61 | 11 |
| 35.8 | 2.51 | 3 |
| 36.6 | 2.46 | 6 |
| 37.6 (sh)* | 2.39 | 14 |
| 37.9 | 2.37 | |
| 39.6 | 2.28 | 4 |
| 40.5 | 2.23 | 2 |
| 42.9 | 2.11 | 5 |
| 44.8 | 2.02 | 2 |
| 45.2 | 2.01 | 4 |
| 46.1 | 1.99 | 6 |
| 48.1 | 1.89 | 2 |
| 49.0 | 1.86 | 4 |
| 50.6 | 1.80 | 3 |

-continued

| 2θ | d | 100 × I/Io |
|---|---|---|
| 54.8 | 1.68 | 4 |

*sh = shoulder (b) A portion of a solid crystalline product exhibiting an X-ray powder diffraction pattern essentially identical to that above was calcined in air at about 200° C. for 2 hours, then at 600° C. overnight. The calcined product had an X-ray powder diffraction pattern characterized by the following data:

| 2θ | d | 100 × I/Io |
|---|---|---|
| 8.0 | 11.1 | 14 |
| 9.8 | 9.03 | 40 |
| 11.7 | 7.56 | 3 |
| 12.75 | 6.94 | 20 |
| 13.65 | 6.49 | 6 |
| 14.7 | 6.03 | 5 |
| 16.1 | 5.50 | 54 |
| 17.55 | 5.05 | 2 |
| 19.5 (sh) | 4.55 | 17 |
| 19.85 | 4.47 | 23 |
| 20.7 | 4.29 | 8 |
| 21.9 | 4.06 | 100 |
| 22.1 (sh) | 4.02 | 44 |
| 22.5 (sh) | 3.95 | 48 |
| 23.5 | 3.79 | 54 |
| 24.0 (sh) | 3.71 | 16 |
| 24.2 (sh) | 3.68 | 10 |
| 25.7 | 3.47 | 20 |
| 25.9 (sh) | 3.44 | 9 |
| 26.7 | 3.34 | 13 |
| 27.3 (sh) | 3.27 | 14 |
| 27.65 | 3.23 | 20 |
| 28.5 | 3.13 | 8 |
| 29.6 | 3.02 | 29 |
| 30.3 | 2.95 | 16 |
| 31.75 | 2.82 | 8 |
| 32.6 | 2.75 | 22 |
| 33.95 | 2.64 | 7 |
| 34.4 (sh) | 2.61 | 5 |
| 35.5 | 2.53 | 9 |
| 37.2 | 2.42 | 8 |
| 38.2 (sh) | 2.36 | 6 |
| 38.8 | 2.32 | 14 |
| 39.4 | 2.29 | 2 |
| 39.7 | 2.27 | 2 |
| 41.0 | 2.20 | 8 |
| 41.4 (sh) | 2.18 | 5 |
| 43.6 | 2.08 | 3 |
| 44.6 | 2.03 | 5 |
| 45.3 | 2.00 | 6 |
| 49.2 | 1.85 | 8 |
| 49.6 | 1.84 | |
| 50.4 | 1.81 | 3 |
| 52.4 | 1.75 | 1 |
| 53.6 | 1.71 | 5 |
| 54.6 | 1.68 | 2 |

(sh = shoulder)

EXAMPLES 33–36 Preparation of AlPO$_4$-11

A procedure similar to that in example 32 was followed except where indicated in Table C below. The composition of each final reaction mixture in molar oxide ratios was:

1.0 R:Al$_2$O$_3$:P$_2$O$_5$:40H$_2$O

The solid product from each reaction contained in each case a phase characterized by an X-ray powder diffraction pattern essentially the same as that of the uncalcined product of example 32.

TABLE C

| EXAMPLE # | R | REACTION TIME (Hrs) | REACTION |
|---|---|---|---|
| 33 | (i-C$_3$H$_7$)$_2$NH | 24 | 200 |
| 34 | (C$_2$H$_5$) (n-C$_4$H$_9$)NH | 24 | 200 |
| 35 | (n-C$_4$H$_9$)$_2$NH | 48 | 200 |
| 36 | (n-C$_5$H$_{11}$)$_2$NH | 24 | 200 |
| 37 | " | 24 | 150 |

The species AlPO$_4$-11 as herein referred to is a crystalline metallophosphate whose essential framework structure has a chemical composition, expressed in terms of molar ratios of oxides, is Al$_2$O$_3$:1.0±0.2 P$_2$O$_5$ and having a characteristic X-ray powder diffraction pattern which contains at least the d-spacings set forth in TABLE 8 below:

TABLE 8

| 2θ | d | 100 × I/Io |
|---|---|---|
| 9.4–9.5 | 9.41–9.31 | 31–49 |
| 20.5–20.6 | 4.33–4.31 | 34–53 |
| 21.0–21.25 | 4.23–4.19 | 100 |
| 22.15–22.25 | 4.01–4.00 | 12–58 |
| 22.5–22.7 | 3.95–3.92 | 47–75 |
| 23.15–23.5 | 3.84–3.79 | 10–68 |

All of the AlPO$_4$-11 compositions for which the X-ray powder diffraction data has presently been obtained have patterns that are within the generalized pattern of TABLE 9 below:

TABLE 9

| 2θ | d | 100 × I/Io |
|---|---|---|
| 8.1–8.2 | 10.9–10.8 | 19–34 |
| 8.5–8.5 | 10.4 | (sh) |
| 9.4–9.5 | 9.41–9.31 | 49–31 |
| 13.2–13.3 | 6.71–6.66 | 11–16 |
| 15.7–15.8 | 5.64–5.61 | 16–30 |
| 16.3–16.4 | 5.44–5.40 | 3–5 |
| 19.0–19.2 | 4.67–4.62 | 4–7 |
| 20.5–20.6 | 4.33–4.31 | 34–53 |
| 21.0–21.25 | 4.23–4.19 | 100 |
| 22.15–22.25 | 4.01–4.00 | 12–58 |
| 22.5–22.7 | 3.95–3.92 | 47–75 |
| 23.15–23.5 | 3.84–3.79 | 10–68 |
| 24.6–24.8 | 3.62–3.59 | 4–10 |
| 24.8–25.0 | 3.59–3.56 | 4–11 |
| 26.3–26.4 | 3.39–3.38 | 11–18 |
| 26.6–26.8 | 3.35–3.33 | 11–18 |
| 28.3–28.5 | 3.15–3.13 | (sh) |
| 28.7–28.9 | 3.11–3.09 | 11–15 |
| 29.1–29.25 | 3.07–3.05 | 5–7 |
| 29.5–29.6 | 3.03–3.02 | 5–9 |
| 31.5–31.6 | 2.84–2.83 | 5–10 |
| 32.8–33.0 | 2.73–2.71 | 6–15 |
| 34.0–34.4 | 2.64–2.61 | 4–13 |
| 35.6–35.9 | 2.52–2.50 | 2–3 |
| 36.6–36.65 | 2.46–2.45 | 4–6 |
| 37.6 | 2.39 | 12 |
| 37.8–38.0 | 2.38–2.37 | 8–15 |
| 39.4–39.7 | 2.29–2.27 | 2–4 |
| 40.5–40.8 | 2.23–2.21 | 2 |
| 42.2–42.5 | 2.14–2.13 | 2–3 |
| 42.7–43.2 | 2.12–2.09 | 4–5 |
| 44.8–45.0 | 2.02–2.01 | 2–4 |
| 45.2–45.5 | 2.01–1.99 | 2–4 |
| 46.0–46.2 | 1.97–1.96 | 2–6 |
| 47.9–48.1 | 1.90–1.89 | 2 |
| 48.9–49.1 | 1.86–1.86 | 2–4 |
| 50.6–51.0 | 1.80–1.79 | 2–3 |
| 54.8–54.85 | 1.68–1.67 | 2–4 |
| 55.5–55.6 | 1.66–1.65 | 2 |

EXAMPLE 37 Preparation of AlPO$_4$-12

A reaction mixture was prepared by combining 46.0 grams of 85% orthophosphoric acid (H$_3$PO$_4$) and 119.2 grams of water, to which was added 27.5 grams of the same hydrated aluminum oxide as in Example 1 (a pseudoboehmite phase, 74.2 wt.% Al$_2$O$_3$, 25.8 wt.% H$_2$O), and stirred until homogeneous. To this mixture was added 6.0 grams of ethylenediamine (C$_2$H$_8$N$_2$), and the mixture stirred until homogeneous. The composition of the final reaction mixture in molar oxide ratios was:

0.5C$_2$H$_8$N$_2$:Al$_2$O$_3$:P$_2$O$_5$:40H$_2$O

The reaction mixture was sealed in a stainless steel pressure vessel lined with polytetrafluoroethylene and heated in an oven at 200° C. at autogenous pressure for 24 hours. The solid reaction product was recovered by filtration, washed with water, and dried in air at room temperature.

Chemical analysis showed 4.3 wt.% C, 4.3 wt.% N, 35.0 wt.% Al$_2$O$_3$, 49.5 wt.% P$_2$O$_5$, 15.4 wt.% LOI, giving a product composition in molar oxide ratios of:

0.52C$_2$H$_8$N$_2$:1.00 Al$_2$O$_3$:1.02 P$_2$O$_5$:0.75H$_2$O

The crystalline AlPO$_4$-12 phase had an X-ray powder diffraction pattern characterized by the following data, wherein "I" is the intensity and "d" the interplanar spacing:

| 2θ | | d | 100 × I/Io |
|---|---|---|---|
| 6.15 | | 14.37 | 25 |
| 11.2 | | 7.90 | 7 |
| 12.3 | | 7.20 | 22 |
| 13.3 | | 6.66 | 56 |
| 14.1 | | 6.28 | 5 |
| 15.2 | | 5.83 | 4 |
| 17.2 | | 5.16 | 20 |
| 18.5 | | 4.80 | 27 |
| 18.9 | | 4.70 | 13 |
| 19.9 | (sh) | 4.46 | — |
| 20.9 | | 4.25 | 100 |
| 22.3 | | 3.99 | 44 |
| 23.05 | | 3.86 | 31 |
| 23.85 | | 3.73 | 55 |
| 25.05 | | 3.55 | 35 |
| 26.5 | | 3.36 | 31 |
| 26.7 | (sh) | 3.34 | |
| 27.95 | (sh) | 3.19 | |
| 28.2 | (sh) | 3.16 | 20 |
| 28.95 | | 3.08 | 11 |
| 29.8 | | 3.00 | 25 |
| 30.4 | (sh) | 2.94 | |
| 30.85 | (sh) | 2.90 | 44 |
| 31.15 | (sh) | 2.87 | |
| 32.55 | | 2.75 | 7 |
| 33.0 | (sh) | 2.71 | 5 |
| 33.2 | (sh) | 2.70 | |
| 34.0 | | 2.64 | 18 |
| 34.8 | | 2.58 | 18 |
| 37.8 | | 2.38 | 4 |
| 38.6 | | 2.33 | 11 |
| 39.3 | | 2.29 | 9 |
| 40.0 | | 2.25 | 7 |
| 40.7 | | 2.22 | 9 |
| 41.8 | | 2.16 | 7 |
| 42.7 | (sh) | 2.12 | — |
| 43.6 | | 2.08 | 5 |
| 44.5 | | 2.04 | 5 |
| 45.6 | | 1.99 | 4 |
| 46.6 | | 1.95 | 7 |
| 48.15 | | 1.89 | 9 |
| 48.6 | | 1.87 | 5 |
| 50.0 | | 1.82 | 5 |
| 51.8 | | 1.76 | 7 |
| 52.7 | | 1.74 | 4 |

-continued

| 2θ | d | 100 × I/Io |
|---|---|---|
| 54.6 | 1.68 | 9 |
| 55.5 | 1.66 | 2 |

(sh = shoulder)

EXAMPLE 38 Preparation of AlPO$_4$-12

A reaction mixture was prepared by combining 76.8 grams of 85% orthophosphoric acid (H$_3$PO$_4$) and 183.7 grams of water, to which was added 45.8 grams of the same hydrated aluminum oxide as in Example 38, and stirred until homogeneous. To this mixture was added 28.7 grams of 2-imidazolidone [(CH$_2$NH)$_2$CO] dissolved in 75 grams of H$_2$O, and the mixture stirred until homogeneous. The composition of the final reaction mixture in molar oxide ratios was:

(CH$_2$NH)$_2$CO:Al$_2$O$_3$:P$_2$O$_5$:50H$_2$O

The reaction mixture was placed in a stainless steel pressure vessel having an inert liner and heated in an oven at 200° C. at autogenous pressure for 169 hours. The solid reaction product was recovered by filtration, washed with water, and dried in air at 110° C. Chemical analysis showed 5.2 wt.% C, 6.2 wt.% N, 33.2 wt.% Al$_2$O$_3$, 48.2 wt.% P$_2$O$_5$, 18.1 wt.% LOI, giving a product composition in molar oxide ratios of:

0.68 (CH$_2$NH)$_2$CO:Al$_2$O$_3$:1.04 P$_2$O$_5$:0.97H$_2$O

The above product was AlPO$_4$-12 as indicated by having an X-ray powder diffraction pattern essentially identical to that in example 37.

The species AlPO$_4$-12 as herein referred to is a crystalline metallophosphate whose essential framework structure has a chemical composition, expressed in terms of molar ratios of oxides, is Al$_2$O$_3$:1.0±0.2 P$_2$O$_5$ and having a characteristic X-ray powder diffraction pattern which contains at least the d-spacings set forth in TABLE 10 below:

TABLE 10

| 2θ | d | 100 × I/Io |
|---|---|---|
| 6.15–6.2 | 14.37–14.26 | 25–48 |
| 13.3–13.35 | 6.66–6.63 | 56–63 |
| 20.9–21.0 | 4.25–4.44 | 100 |
| 22.3–22.4 | 3.99–3.97 | 33–45 |
| 23.85–24.0 | 3.73–3.71 | 46–61 |
| 30.85–30.95 | 2.90–2.89 | 34–44 |

All of the AlPO$_4$-12 compositions for which the X-ray powder diffraction data has presently been obtained have patterns that are within the generalized pattern of Table 11 below:

TABLE 11

| 2θ | d | I/Io × 100 |
|---|---|---|
| 6.15–6.2 | 14.37–14.26 | 48–25 |
| 11.2–11.3 | 7.90–7.83 | 15–7 |
| 12.3–12.35 | 7.20–7.17 | 34–22 |
| 13.3–13.35 | 6.66–6.63 | 63–56 |
| 14.1–14.15 | 6.28–6.26 | 8–5 |
| 15.2 | 5.83 | 4–1 |
| 17.2–17.3 | 5.16–5.13 | 29–20 |
| 18.4–18.6 | 4.82–4.77 | 37–27 |
| 18.9 | 4.70 | 16–13 |
| 19.9 | 4.46 | SH |
| 20.9–21.0 | 4.25–4.23 | 100 |
| 21.65–21.85 | 4.10–4.07 | 14–13 |
| 22.3–22.4 | 3.99–3.97 | 45–33 |
| 22.6 SH | 3.93 | 14 |
| 23.0–23.05 | 3.87–3.86 | 31–9 |
| 23.85–24.0 | 3.73–3.71 | 61–46 |
| 25.05–25.2 | 3.55–3.53 | 35–25 |
| 26.5–26.6 | 3.36–3.35 | 35–31 |
| 26.7–26.8 | 3.34–3.33 | SH |
| 27.95–28.0 | 3.19–3.19 | 6–5 |
| 28.2–28.3 | 3.16–3.15 | SH |
| 28.95–29.0 | 3.08–3.08 | 13–10 |
| 29.8–30.0 | 3.00–2.98 | 25–20 |
| 30.4 | 2.94 | SH |
| 30.85–30.95 | 2.90–2.89 | 44–34 |
| 31.1–31.2 | 2.88–2.87 | SH |
| 32.55–32.6 | 2.75–2.75 | 7–6 |
| 33.0–33.1 | 2.71–2.71 | 6–5 |
| 33.2–33.4 | 2.70–2.68 | SH |
| 34.0–34.1 | 2.64–2.63 | 18–17 |
| 34.8–34.95 | 2.58–2.57 | 19–18 |
| 35.4–35.5 | 2.54–2.53 | SH |
| 36.2 | 2.48 | 4–1 |
| 37.0 | 2.43 | 1–0 |
| 37.4 | 2.40 | 4–0 |
| 37.6–37.8 | 2.39–2.38 | 4–0 |
| 37.9 | 2.37 | SH |
| 38.3 | 2.35 | SH |
| 38.6–38.65 | 2.33–2.33 | 11–8 |
| 39.3–39.4 | 2.29–2.29 | 9–7 |
| 40.0 | 2.25 | 8–7 |
| 40.7–40.8 | 2.22–2.21 | 9–7 |
| 41.8–41.9 | 2.16–2.16 | 7–5 |
| 42.6–42.7 | 2.12–2.12 | SH |
| 43.6–43.8 | 2.08–2.07 | 7–5 |
| 44.5–44.7 | 2.04–2.03 | 5–3 |
| 45.6–45.7 | 1.99–1.99 | 4–2 |
| 46.5–46.6 | 1.95–1.95 | 7–2 |
| 48.0–48.15 | 1.90–1.89 | 9–4 |
| 48.6–48.7 | 1.87–1.87 | 5–4 |
| 50.0–50.2 | 1.82–1.82 | 8–5 |
| 51.8 | 1.76 | 8–7 |
| 52.7–5.29 | 1.74–1.73 | 4–2 |
| 54.6 | 1.68 | 9–8 |
| 55.5 | 1.66 | 2 |

EXAMPLE 39 Preparation of AlPO$_4$-14

(a) A reaction mixture was prepared by combining 57.7 grams of 85% orthophosphoric acid (H$_3$PO$_4$) and 100 grams of water, to which was added 34.4 grams of a hydrated aluminum oxide (74.2 wt.% Al$_2$O$_3$, 25.8 wt.% H$_2$O), and stirred until homogeneous. To this mixture was added 18.3 grams of t-butylamine (t-BuNH$_2$) and then 49.1 grams of water, and the mixture stirred until homogeneous. The composition of the final reaction mixture in molar oxide ratios was:

1.0 t-BuNH$_2$:Al$_2$O$_3$:P$_2$O$_5$:40H$_2$O

The reaction mixture was sealed in a stainless steel pressure vessel having an inert plastic lining and heated in an oven at 150° C. at autogenous pressure for 96 hours. The solid reaction product was recovered by filtration, washed with water, and dried in air at 110° C. Chemical analysis indicated the product contained 7.2 wt.% C, 2.6 wt.% N, 34.3 wt.% Al$_2$O$_3$, 47.7 wt.% P$_2$O$_5$, 17.5 wt.% LOI, giving a product composition in molar oxide ratios of:

0.49 t-BuNH$_2$:1.00 Al$_2$O$_3$:1.00 P$_2$O$_5$:0.91H$_2$O

The above product had an X-ray powder diffraction pattern characterized by the following data, wherein "I" is the intensity and "d" the interplanar spacing:

| 2θ | d | 100 × I/Io |
|---|---|---|
| 9.2 | 9.61 | 100 |
| 9.4 | 9.41 | (sh) |
| 11.2 | 7.90 | 18 |
| 13.1 | 6.76 | 17 |
| 13.4 | 6.61 | (sh) |

| 2θ | d | 100 × I/Io |
|---|---|---|
| 14.8 | 5.98 | 3 |
| 15.8 | 5.61 | 23 |
| 18.0 | 4.93 | 12 |
| 18.8 | 4.72 | 1 |
| 19.2 | 4.62 | 1 |
| 20.9 | 4.25 | 5 |
| 21.6 | 4.11 | 10 |
| 22.2 | 4.00 | 22 |
| 22.7 | 3.92 | 36 |
| 23.4 | 3.80 | 1 |
| 23.7 | 3.75 | 1 |
| 25.2 | 3.54 | 2 |
| 26.1 | 3.41 | 20 |
| 27.1 | 3.29 | 9 |
| 27.7 | 3.22 | 2 |
| 28.5 | 3.13 | 5 |
| 29.5 | 3.03 | 12 |
| 30.2 | 2.96 | 8 |
| 30.5 | 2.93 | (sh) |
| 30.9 | 2.89 | 4 |
| 31.2 | 2.87 | (sh) |
| 32.0 | 2.80 | 1 |
| 32.4 | 2.76 | 1 |
| 33.2 | 2.70 | (sh) |
| 33.5 | 2.67 | 6 |
| 34.1 | 2.63 | 1 |
| 35.0 | 2.56 | 1 |
| 35.5 | 2.53 | 2 |
| 36.4 | 2.47 | 3 |
| 38.1 | 2.36 | 3 |
| 38.8 | 2.32 | 5 |
| 39.5 | 2.28 | 1 |
| 40.4 | 2.23 | 5 |
| 40.8 | 2.21 | 1 |
| 42.0 | 2.15 | 2 |
| 42.4 | 2.13 | 2 |
| 43.6 | 2.08 | 1 |
| 44.0 | 2.06 | 3 |
| 44.8 | 2.02 | 3 |
| 45.9 | 1.98 | 2 |
| 46.3 | 1.96 | 2 |
| 47.8 | 1.90 | 2 |
| 48.5 | 1.88 | 2 |
| 49.8 | 1.83 | 1 |
| 51.6 | 1.77 | 2 |
| 52.7 | 1.74 | 1 |
| 53.5 | 1.71 | 4 |
| 55.7 | 1.65 | 2 |

(sh = shoulder)

The product was designated AlPO$_4$-14.

(b) A portion of the solid crystalline product obtained above was calcined in air at about 550° C. for 2 hours. The calcined product had an X-ray powder diffraction pattern characterized by the following data:

| 2θ | d | 100 × I/Io |
|---|---|---|
| 9.0 | 9.83 | 100 |
| 9.6 | 9.21 | (sh) |
| 11.5 | 7.69 | 29 |
| 12.0 | 7.38 | 9 |
| 13.2 | 6.71 | 45 |
| 13.3 | 6.66 | (sh) |
| 13.6 | 6.51 | 32 |
| 14.3 | 6.19 | 10 |
| 14.8 | 5.99 | 5 |
| 16.0 | 5.54 | 10 |
| 16.2 | 5.47 | (sh) |
| 16.8 | 5.28 | 2 |
| 18.2 | 4.87 | 35 |
| 18.6 | 4.77 | 38 |
| 18.9 | 4.70 | (sh) |
| 19.9 | 4.46 | 5 |
| 20.7 | 4.29 | 9 |
| 20.9 | 4.25 | 9 |
| 21.6 | 4.11 | (sh) |
| 22.0 | 4.04 | 23 |
| 22.5 | 3.95 | 29 |
| 22.8 | 3.90 | (sh) |
| 23.2 | 3.83 | 7 |
| 23.5 | 3.79 | 6 |
| 24.2 | 3.68 | 3 |
| 24.8 | 3.59 | (sh) |
| 25.1 | 3.55 | 6 |
| 25.9 | 3.44 | 3 |
| 26.6 | 3.35 | 12 |
| 27.0 | 3.30 | 20 |
| 27.4 | 3.25 | 16 |
| 27.8 | 3.21 | 11 |
| 28.0 | 3.19 | 11 |
| 28.6 | 3.12 | (sh) |
| 29.2 | 3.06 | 11 |
| 29.7 | 3.01 | 20 |
| 30.4 | 2.94 | 14 |
| 31.0 | 2.88 | 9 |
| 32.3 | 2.77 | 4 |
| 33.0 | 2.71 | 6 |
| 33.9 | 2.64 | 4 |
| 34.8 | 2.58 | 4 |
| 35.6 | 2.52 | 2 |
| 36.8 | 2.44 | 5 |
| 37.7 | 2.39 | 3 |
| 38.4 | 2.34 | 2 |
| 39.1 | 2.30 | 3 |
| 40.1 | 2.25 | 3 |
| 40.6 | 2.22 | 3 |
| 41.8 | 2.16 | 1 |
| 42.6 | 2.12 | 3 |
| 43.0 | 2.10 | 2 |
| 44.2 | 2.05 | 6 |
| 45.3 | 2.00 | 1 |
| 46.2 | 1.95 | 2 |
| 47.4 | 1.92 | 2 |
| 48.6 | 1.87 | 3 |
| 50.0 | 1.82 | 3 |
| 52.1 | 1.76 | 3 |
| 54.1 | 1.70 | 4 |

EXAMPLE 40 Preparation of AlPO$_4$-14

A reaction mixture was prepared by combining 46.1 grams of 85% orthophosphoric acid (H$_3$PO$_4$) and 119.2 grams of water, to which was added 27.5 grams of the same hydrated aluminum oxide as in Example 27 and stirred until homogeneous. To this mixture was added 11.8 grams of isopropylamine (i-PrNH$_2$), and the mixture stirred until homogeneous. The composition of the final reaction mixture in molar oxide ratios was:

1.0 i-PrNH$_2$:Al$_2$O$_3$:P$_2$O$_5$:40H$_2$O

The reaction mixture was sealed in a stainless steel pressure vessel lined with an inert plastic material (polytetrafluoroethylene) and heated in an oven at 200° C. at autogenous pressure for 24 hours. The solid reaction product was recovered by filtration, washed with water, and dried in air at room temperature. Chemical analysis of the product showed 6.0 wt.% C, 2.4 wt.% N, 34.8 wt.% Al$_2$O$_3$, 48.6 wt.% P$_2$O$_5$, 16.1 wt.% LOI, giving a product composition in molar oxide ratios of:

0.49 i-PrNH$_2$:1.00Al$_2$O$_3$:1.00 P$_2$O$_5$:1.03H$_2$O

The above product was established to be AlPO$_4$-14 by virtue of having an X-ray powder diffraction pattern essentially identical to that of the uncalcined product in example 39.

The species AlPO$_4$-14 as herein referred to is a crystalline metallophosphate whose essential framework structure has a chemical composition, expressed in terms of molar ratios of oxides, is Al$_2$O$_3$:1.0±0.2 P$_2$O$_5$ and having a characteristic X-ray powder diffraction pattern which contains at least the d-spacings set forth in Table 12 below:

TABLE 12

| 2θ | d | 100 × I/Io |
|---|---|---|
| 8.9–9.2 | 9.94–9.61 | 100–100 |
| 11.1–11.2 | 7.97–7.90 | 18–28 |
| 13.05–13.1 | 6.78–6.76 | 17–23 |
| 15.8–15.85 | 5.61–5.59 | 21–23 |
| 22.2–22.3 | 4.00–3.99 | 22–28 |
| 22.7 | 3.92 | 36–49 |
| 26.1–26.2 | 3.44–3.40 | 20–25 |

All of the AlPO$_4$-14 compositions for which the X-ray powder diffraction data has presently been obtained have patterns that are within the generalized pattern of TABLE 12(a) below:

TABLE 12(a)

| 2θ | d | 100 × I/Io |
|---|---|---|
| 8.9–9.2 | 9.94–9.61 | 100–>100 |
| 9.4 | 9.41 | (sh) |
| 11.1–11.2 | 7.97–7.90 | 18–28 |
| 13.1 | 6.76 | 17–23 |
| 13.4 | 6.61 | (sh)–9 |
| 14.8 | 5.98 | 3 |
| 15.8–15.85 | 5.61–5.59 | 21–23 |
| 18.0 | 4.93 | 12–20 |
| 18.8 | 4.72 | 1–2 |
| 19.2 | 4.62 | 1 |
| 20.9 | 4.25 | 5–10 |
| 21.6–21.9 | 4.11–4.06 | 5–10 |
| 22.2–22.3 | 4.00–3.99 | 22–28 |
| 22.7 | 3.92 | 36–49 |
| 23.4 | 3.80 | 1 |
| 23.7–23.85 | 3.75–3.73 | 1–2 |
| 25.2–25.45 | 3.54–3.50 | 2–4 |
| 26.1–26.2 | 3.41–3.40 | 20–25 |
| 27.1–27.2 | 3.29–3.28 | 6–9 |
| 27.7 | 3.22 | 2–4 |
| 28.5–28.85 | 3.13–3.09 | (sh)–5 |
| 29.5–29.6 | 3.03–3.02 | 12–20 |
| 30.2–30.3 | 2.96–2.95 | 8–11 |
| 30.5 | 2.93 | (sh) |
| 30.9 | 2.89 | 4–18 |
| 31.2–31.3 | 2.87–2.86 | (sh) |
| 32.0–32.2 | 2.80–2.78 | 1–3 |
| 32.4–32.6 | 2.76–2.75 | 1–3 |
| 33.2–33.3 | 2.70–2.69 | (sh)–3 |
| 33.5–33.8 | 2.67–2.65 | 6–8 |
| 34.1 | 2.63 | 1 |
| 35.0–35.2 | 2.56–2.55 | 1–3 |
| 35.5–35.7 | 2.53–2.51 | 2–5 |
| 36.4–36.6 | 2.47–2.46 | 3–4 |
| 37.3 | 2.41 | 1 |
| 38.0–38.1 | 2.37–2.36 | 1–3 |
| 38.5–38.8 | 2.34–2.32 | 2–5 |
| 39.1–39.5 | 2.30–2.28 | (sh)–4 |
| 40.4–40.5 | 2.23–2.23 | 4–5 |
| 40.8–41.0 | 2.21–2.20 | 2–4 |
| 42.4 | 2.13 | 2–3 |
| 42.8 | 2.11 | 2 |
| 43.6 | 2.08 | 1 |
| 44.0–44.2 | 2.06–2.05 | 3 |
| 44.6–44.8 | 2.03–2.02 | 3 |
| 45.0 | 2.01 | 3 |
| 45.9 | 1.98 | 2 |
| 46.2–46.3 | 1.96–1.96 | 2 |
| 46.6 | 1.95 | 3 |
| 47.8–48.0 | 1.90–1.90 | 2–3 |
| 48.5–48.7 | 1.88–1.87 | 2–3 |
| 49.8–50.0 | 1.83–1.82 | 1–2 |
| 51.6–52.0 | 1.77–1.76 | 2–3 |
| 52.7–52.8 | 1.73–1.74 | 1–2 |
| 53.5–54.1 | 1.71–1.70 | 4 |
| 55.2–55.7 | 1.66–1.65 | 1–2 |

(sh = shoulder)

EXAMPLE 41 Preparation of AlPO$_4$-16

(a) A reaction mixture was prepared by combining 57.7 grams of 85% orthophosphoric acid (H$_3$PO$_4$) and 69.6 grams of water, to which was added 34.4 grams of a hydrated aluminum oxide (a pseudo-boehmite phase, 74.2 wt.% Al$_2$O$_3$, 25.8 wt.% H$_2$O), and stirred until homogeneous. To this mixture was added 27.8 grams of quinuclidine (C$_7$H$_{13}$N) dissolved in 50.4 grams of water, and then 29.1 grams of water and the mixture stirred until homogeneous. The composition of the final reaction mixture in molar oxide ratios was:

1.0C$_7$H$_{13}$N:Al$_2$O$_3$:P$_2$O$_5$:40H$_2$O

The reaction mixture was sealed in a stainless steel pressure vessel lined with an inert plastic material and heated in an oven at 150° C. at autogenous pressure for 48 hours. The solid reaction product was recovered by filtration, washed with water, and dried in air at 110° C. Chemical analysis of the product indicated the presence of 7.6 wt.% C, 1.33 wt.% N, 32.4 wt.% Al$_2$O$_3$, 43.4 wt.% P$_2$O$_5$, 24.1 wt.% LOI, giving a product composition in molar oxide ratios of:

0.28C$_7$H$_{13}$N:1.00 Al$_2$O$_3$:0.96 P$_2$O$_5$:2.45H$_2$O

The above product had an X-ray powder diffraction pattern characterized by the following data wherein "I" is the intensity and "d" the interplanar spacing:

| 2θ | d | 100 × I/Io |
|---|---|---|
| 11.3 | 7.83 | 62 |
| 15.5 | 5.72 | 2 |
| 17.3 | 5.13 | 2 |
| 18.7 | 4.75 | 50 |
| 21.9 | 4.06 | 100 |
| 22.95 | 3.875 | 9 (sh) |
| 26.55 | 3.357 | 27 |
| 27.6 | 3.23 | 2 |
| 28.0 | 3.19 | 2 |
| 29.0 | 3.08 | 12 |
| 29.75 | 3.00 | 28 |
| 32.7 | 2.739 | 4 |
| 34.7 | 2.585 | 5 |
| 37.9 | 2.374 | 8 |
| 39.6 | 2.276 | 2 |
| 44.2 | 2.049 | 2 |
| 48.5 | 1.877 | 6 |
| 52.4 | 1.746 | 3 |
| 54.8 | 1.675 | 3 |

The product was designated AlPO$_4$-16.

(b) Using the same procedure and reaction mixture composition as in part (a) except that the proportion of quinuclidine was decreased by 50 percent and the mixture was heated at 200° C. for 24 hours, AlPO$_4$-16 was again produced. A small amount of AlPO$_4$-17 was also present as an impurity.

(c) The procedure and gel composition of part (a) were followed except that the reaction mixture was heated for 16 hours. A portion of the solids was submitted for X-ray analysis. The above product was established to be AlPO$_4$-16 by virtue of having a powder diffraction pattern essentially identical with that in part (a).

(d) A portion of the solid crystalline product obtained above was calcined in air from 200° C. to 500° C. during 1 hour and then at about 500° C. for 2 hours. The calcined product had an X-ray powder diffraction pattern essentially identical to that in part (c).

The species AlPO$_4$-16 as herein referred to is a crystalline metallophosphate whose essential framework structure has a chemical composition, expressed in terms of molar ratios of oxides, is $Al_2O_3:1.0\pm0.2\ P_2O_5$ and having a characteristic X-ray powder diffraction pattern which contains at least the d-spacings set forth in Table 13 below:

TABLE 13

| $2\theta$ | d | $100 \times I/I_o$ |
|---|---|---|
| 11.3–11.5 | 7.83–7.69 | 59–63 |
| 18.7–18.85 | 4.75–4.71 | 48–54 |
| 21.9–22.2 | 4.06–4.00 | 100 |
| 26.55–26.75 | 3.36–3.33 | 23–27 |
| 29.75–29.95 | 3.00–2.98 | 26–30 |

All of the AlPO₄-16 compositions for which the X-ray powder diffraction data has presently been obtained have patterns that are within the generalized pattern of Table 14 below:

TABLE 14

| $2\theta$ | d | $100 \times I/I_o$ |
|---|---|---|
| 11.3–11.5 | 7.83–7.69 | 59–63 |
| 15.5–15.9 | 5.72–5.57 | 0–2 |
| 17.3–17.4 | 5.13–5.10 | 0–2 |
| 18.7–18.85 | 4.75–4.71 | 48–54 |
| 21.9–22.2 | 4.06–4.00 | 100 |
| 22.95–23.1 | 3.875–3.850 | 9–11 |
| 26.55–26.75 | 3.357–3.332 | 23–27 |
| 27.4–27.6 | 3.255–3.232 | 0–2 |
| 28.0–28.2 | 3.187–3.164 | 0–2 |
| 29.0–29.1 | 3.079–3.058 | 8–15 |
| 29.75–29.95 | 3.003–2.983 | 26–30 |
| 32.7–32.9 | 2.739–2.722 | 4–5 |
| 34.7–34.95 | 2.585–2.567 | 5–7 |
| 37.9–38.1 | 2.374–2.362 | 8–10 |
| 39.6–40.0 | 2.276–2.254 | 0–2 |
| 44.2–44.5 | 2.049–2.036 | 2–3 |
| 48.5–48.7 | 1.877–1.870 | 6–8 |
| 52.4–52.6 | 1.746–1.740 | 2–3 |
| 54.8–55.0 | 1.675–1.670 | 2–3 |

EXAMPLE 42 Preparation of AlPO₄-17

(a) A reaction mixture was prepared by combining 56.7 grams of 85% orthophosphoric acid ($H_3PO_4$) and 69.6 grams of water, to which was added 34.4 grams of a hydrated aluminum oxide (a pseudo-boehmite phase, 74.2 wt.% $Al_2O_3$, 35.8 wt.% $H_2O$), and stirred until homogeneous. To this mixture was added 27.8 grams of quinuclidine ($C_7H_{13}N$) dissolved in 50.4 grams of water, and then 29.1 grams of water, and the mixture stirred until homogeneous. The composition of the final reaction mixture in molar oxide ratios was:

$1.0C_7H_{13}N:Al_2O_3:P_2O_5:40H_2O$

The reaction mixture was placed in a sealed stainless steel pressure vessel lined with an inert plastic material (polytetrafluoroethylene) and heated in an oven at 200° C. at autogenous pressure for 96 hours. The solid reaction product was recovered and washed by repeated centrifugation with water, and dried in air at 110° C. Chemical analysis showed 12.4 wt.% C, 2.2 wt.% N, 32.5 wt.% $Al_2O_3$, 45.9 wt.% $P_2O_5$, 21.4 wt.% LOI, giving a product composition in molar oxide ratios of:

$0.46C_7H_{13}N:1.00\ Al_2O_4:0.99\ P_2O_5:0.87H_2O$

The above product, denominated AlPO₄-17 had an X-ray powder diffraction pattern characterized by the following data, wherein "I" is the intensity and "d" the interplanar spacing:

| $2\theta$ | d | $100 \times I/I_o$ |
|---|---|---|
| 7.65 | 11.55 | 100 |
| 9.7 | 9.12 | 41 |
| 11.35 | 7.79 | 2 |
| 11.9 | 7.44 | 3 |
| 13.35 | 6.63 | 39 |
| 14.2 | 6.24 | 13 |
| 14.7 | 6.03 | 2 |
| 15.4 | 5.75 | 62 |
| 16.6 | 5.34 | 33 |
| 18.0 | 4.93 | 20 |
| 18.8 | 4.72 | 2 |
| 19.6 | 4.53 | 67 |
| 20.5 | 4.33 | 93 |
| 21.4 | 4.15 | 50 |
| 22.1 | 4.02 | 2 |
| 22.5 | 3.95 | 15 |
| 23.3 | 3.82 | 34 |
| 23.8 | 3.74 | 39 |
| 24.2 | 3.68 | 3 |
| 25.3 | 3.52 | 55 |
| 26.95 | 3.38 | 35 |
| 27.4 | 3.26 | 20 |
| 28.05 | 3.18 | 5 |
| 28.7 | 3.11 | 20 |
| 30.6 | 2.92 | 17 |
| 31.2 | 2.87 | 29 |
| 31.8 | 2.81 | 68 |
| 32.4 | 2.76 | 2 |
| 33.5 | 2.67 | 18 |
| 34.0 | 2.64 | 2 |
| 34.6 | 2.59 | 2 |
| 35.15 | 2.55 | 2 |
| 35.9 | 2.50 | 7 |
| 36.4 | 2.47 | 6 |
| 36.8 | 2.44 | 2 |
| 37.3 | 2.41 | 2 |
| 38.0 | 2.37 | 3 |
| 39.4 | 2.29 | 2 |
| 39.8 | 2.26 | 7 |
| 40.4 | 2.23 | 4 |
| 41.2 | 2.19 | 3 |
| 42.2 | 2.14 | 3 |
| 42.8 | 2.11 | 1 |
| 43.6 | 2.08 | 9 |
| 44.45 | 2.04 | 2 |
| 45.75 | 1.98 | 5 |
| 46.2 | 1.96 | 1 |
| 46.6 | 1.95 | 4 |
| 47.8 | 1.90 | 3 |
| 48.6 | 1.87 | 2 |
| 49.25 | 1.85 | 8 |
| 49.65 | 1.84 | 11 |
| 50.2 | 1.82 | 2 |
| 51.25 | 1.78 | 1 |
| 52.0 | 1.76 | 11 |
| 53.2 | 1.72 | 1 |
| 53.85 | 1.70 | 5 |
| 55.45 | 1.66 | 8 |

(b) A portion of the solid crystalline product obtained after continuing the digestion of the above reaction mixture to 168 hours exhibited an X-ray powder diffraction pattern essentially identical to that above.

(c) A portion of the product from part (b) calcined in air at about 550° C. for 2 hours. The calcined product had an X-ray powder diffraction pattern characterized by the following data:

| $2\theta(°)$ | d(A) | $100 \times I/I_o$ |
|---|---|---|
| 7.7 | 11.5 | 77 |
| 9.7 | 9.1 | 46 |
| 11.6 | 7.63 | } 13 |
| 11.85 | 7.47 |  |
| 13.45 | 6.58 | 100 |
| 14.0 | 6.33 | 21 |

-continued

| 2θ(°) | d(Å) | 100 × I/Io |
|---|---|---|
| 14.2 | 6.24 | 28 |
| 14.8 | 5.99 | 2 |
| 15.6 | 5.68 | 16 |
| 16.8 | 5.28 | 6 |
| 18.0 | 5.22 | 3 |
| 19.2 | 4.62 | 5 |
| 19.65 | 4.52 | 12 |
| 20.5 | 4.33 | } 42 |
| 20.8 | 4.27 | |
| 21.6 | 4.11 | 22 |
| 22.2 | 4.00 | 2 |
| 22.6 | 3.93 | 2 |
| 23.65 | 3.76 | } 29 |
| 23.95 | 3.72 | |
| 24.4 | 3.65 | } 22 |
| 24.6 | 3.63 | |
| 25.0 | 3.56 | 7 |
| 25.3 | 3.52 | 12 |
| 26.2 | 3.40 | 7 |
| 27.3 | 3.26 | 20 |
| 28.2 | 3.16 | 15 |
| 28.8 | 3.10 | 10 |
| 29.4 | 3.038 | } 7 |
| 29.6 | 3.018 | |
| 30.1 | 2.969 | 7 |
| 30.8 | 2.903 | 7 |
| 31.4 | 2.849 | 24 |
| 31.9 | 2.805 | } 15 |
| 32.1 | 2.788 | |
| 33.7 | 2.660 | 11 |
| 35.2 | 2.550 | 1 |
| 36.1 | 2.488 | } 7 |
| 36.35 | 2.471 | |
| 39.6 | 2.281 | 2 |
| 41.3 | 2.186 | 3 |
| 42.0 | 2.151 | 2 |
| 42.7 | 2.118 | 4 |
| 43.8 | 2.067 | 1 |
| 44.9 | 2.019 | 1 |
| 46.1 | 1.973 | 1 |
| 46.6 | 1.953 | 2 |
| 47.4 | 1.972 | 3 |
| 48.0 | 1.895 | 2 |
| 49.2 | 1.852 | 2 |
| 50.2 | 1.817 | 7 |
| 51.3 | 1.781 | 7 |
| 52.8 | 1.734 | 2 |
| 54.0 | 1.698 | 1 |
| 55.3 | 1.661 | 2 |

EXAMPLE 43 Preparation of AlPO$_4$-17

A reaction mixture was prepared by combining 115.3 grams of 85% orthophosphoric acid (H$_3$PO$_4$) and 256 grams of water, to which was added 68.7 grams of a hydrated aluminum oxide (a pseudo-boehmite phase, 74.2 wt.% Al$_2$O$_3$, 25.8 wt.% H$_2$O), and stirred until homogeneous. To this mixture was added 43.6 grams of neopentylamine (C$_5$H$_{13}$N) and then 44.1 grams of water, and the mixture stirred until homogeneous. The composition of the final reaction mixture in molar oxide ratios was:

1.0C$_5$H$_{13}$N:Al$_2$O$_3$:P$_2$O$_5$:40H$_2$O

The reaction mixture was placed in a stainless steel pressure vessel lined with an inert plastic material (polytetrafluoroethylene) and heated in an oven at 150° C. at autogenous pressure for 168 hours. The solid reaction product was recovered and washed with repeated centrifugation with water, and dried in air at 110° C. Chemical analysis showed 9.9 wt.% C, 2.5 wt.% N, 32.6 wt.% Al$_2$O$_3$, 44.2 wt.% P$_2$O$_5$, 21.8 wt.% LOI, giving a product composition in molar oxide ratios of:

0.52C$_5$H$_{13}$N:1.00 Al$_2$O$_3$:0.97 P$_2$O$_5$:1.28H$_2$O

The major phase in the above product had an X-ray powder diffraction pattern very similar to that of the product in example 42 (a). The product was designated AlPO$_4$-17.

EXAMPLES 44–45 Preparation of AlPO$_4$-17.

A procedure similar to that in example 42 was followed except where indicated in Table D. The composition of each final reaction mixture in molar oxide ratios was:

1.0 R:Al$_2$O$_3$:P$_2$O$_5$:40H$_2$O where R is indicated in Table D. A portion of the solid product from each reaction was subjected to X-ray analysis and in each case a phase characterized by an X-ray powder diffraction pattern essentially the same as that of the product of example 42 (a) was observed.

TABLE D

| EXAMPLE # | R | REACTION TIME(Hrs) | REACTION TEMP. (°C.) |
|---|---|---|---|
| 44 | Cyclohexylamine | 168 | 200 |
| 45 | Piperidine | 168 | 200 |

The species AlPO$_4$-17 as herein referred to is a crystalline metallophosphate whose essential framework structure has a chemical composition, expressed in terms of molar ratios of oxides, is Al$_2$O$_3$:1.0±0.2 P$_2$O$_5$ and having a characteristic X-ray powder diffraction pattern which contains at least the d-spacings set forth in Table 15 below:

TABLE 15

| 2θ | d | 100 × I/Io |
|---|---|---|
| 7.6–7.8 | 11.6–11.33 | 100 |
| 13.25–13.5 | 6.68–6.56 | 39–54 |
| 15.35–15.6 | 5.77–5.68 | 26–62 |
| 19.55–19.75 | 4.54–4.50 | 14–67 |
| 20.35–20.65 | 4.36–4.30 | 45–93 |
| 21.25–21.5 | 4.18–4.13 | 20–50 |
| 25.3–25.45 | 3.52–3.50 | 12–55 |
| 31.65–31.85 | 2.83–2.81 | 19–68 |

All of the AlPO$_4$-17 compositions for which the X-ray powder diffraction data has presently been obtained have patterns that are within the generalized pattern of Table 16 below:

TABLE 16

| 2θ | d | 100 × I/Io |
|---|---|---|
| 7.6–7.8 | 11.6–11.33 | 100 |
| 9.7–9.9 | 9.12–8.93 | 15–41 |
| 11.35–11.9 | 7.80–7.44 | 4–5 |
| 13.25–13.5 | 6.68–6.56 | 39–54 |
| 14.2–14.4 | 6.24–6.15 | 2–13 |
| 15.35–15.6 | 5.77–5.68 | 26–62 |
| 16.5–16.7 | 5.37–5.31 | 10–33 |
| 17.9–18.15 | 4.96–4.89 | 4–20 |
| 19.55–19.75 | 4.54–4.50 | 14–67 |
| 20.35–20.65 | 4.36–4.30 | 45–93 |
| 21.25–21.5 | 4.18–4.13 | 20–50 |
| 21.7–21.8 | 4.10–4.08 | (sh) |
| 22.5–22.65 | 3.95–3.93 | 3–15 |
| 23.1–23.45 | 3.85–3.79 | 17–34 |
| 23.7–23.95 | 3.75–3.72 | 14–39 |
| 24.1–24.2 | 3.69–3.68 | (sh) |
| 25.3–25.45 | 3.52–3.50 | 12–55 |
| 26.75–27.0 | 3.33–3.30 | 14–35 |
| 27.35–27.5 | 3.26–3.24 | 5–20 |

TABLE 16-continued

| 2θ | d | 100 × I/Io |
|---|---|---|
| 27.85–28.2 | 3.20–3.16 | 2–5 |
| 28.6–28.8 | 3.12–3.10 | 5–20 |
| 29.45–29.8 | 3.03–3.00 | 2–1 |
| 30.45–30.7 | 2.94–2.91 | 4–17 |
| 31.0–31.3 | 2.88–2.86 | 13–29 |
| 31.65–31.85 | 2.83–2.81 | 19–68 |
| 32.3–32.4 | 2.77–2.76 | 1–2 |
| 33.4–33.6 | 2.68–2.67 | 18–8 |
| 34.0 | 2.64 | 2 |
| 34.6 | 2.59 | 2 |
| 35.15 | 2.55 | 2 |
| 35.7–36.0 | 2.51–2.49 | 4–7 |
| 36.3–36.6 | 2.47–2.45 | 1–6 |
| 36.8 | 2.44 | 2 |
| 37.3 | 2.41 | 2 |
| 37.8–38.0 | 2.38 | 1–3 |
| 39.2–39.4 | 2.30 | 2 |
| 39.65–39.9 | 2.27–2.26 | 2–7 |
| 40.3–40.5 | 2.24–2.23 | 1–4 |
| 41.0–41.2 | 2.20–2.19 | 1–3 |
| 41.9–42.2 | 2.16–2.14 | 1–3 |
| 42.8 | 2.11 | 1 |
| 43.6–43.8 | 2.08–2.07 | 2–9 |
| 44.45 | 2.04 | 2 |
| 45.5–45.8 | 1.99–1.98 | 1–5 |
| 46.2 | 1.97 | 1 |
| 46.5–46.7 | 1.95–1.95 | 1–4 |
| 47.35–47.8 | 1.92–1.90 | 1–3 |
| 48.55–48.8 | 1.88–1.87 | 1–2 |
| 49.25 | 1.85 | 8 |
| 49.45–49.7 | 1.84–1.83 | 4–11 |
| 50.2–5025 | 1.82–1.82 | 1–2 |
| 51.25 | 1.78 | 1 |
| 52.0–52.2 | 1.76–1.75 | 3–11 |
| 53.1–53.2 | 1.72–1.72 | 1 |
| 53.75–54.0 | 1.71–1.70 | 1–5 |
| 55.2–55.5 | 1.66–1.66 | 3–8 |

(sh = shoulder)

EXAMPLE 46 Preparation of AlPO₄-18

A reaction mixture was prepared by combining 46.1 grams of 85% orthophosphoric acid ($H_3PO_4$) and 53.8 grams of water, to which was added 27.5 grams of a pseudo-boehmite phase, (74.2 wt.% $Al_2O_3$, 25.8 wt.% $H_2O$), and stirred until homogeneous. To this mixture was added an aqueous solution prepared by combining 6.5 grams of 37 wt.% HCl and 98.0 grams of 40 wt.% tetraethylammonium hydroxide (TEAOH), and the mixture stirred until homogeneous. The composition of the final reaction mixture in molar oxide ratios was:

0.33HCl:0.67(TEA)₂O:Al₂O₃.P₂O₅:40H₂O

The reaction mixture was placed in a sealed stainless steel pressure vessel lined with an inert plastic material (polytetrafluoroethylene) and heated in an oven at 150° C. at autogenous pressure for 336 hours. The solid reaction product was recovered by filtration, washed with water, and dried in air at room temperature. Chemical analysis showed 8.9 wt.% C, 1.28 wt.% N, 33.5 wt.% Al₂O₃, 38.9 wt.% P₂O₅, 26.4 wt.% LOI, giving a product composition in molar oxide ratios of:

0.14(TEA)₂O:1.00 Al₂O₃:0.83 P₂O₅:0.9H₂O

The above product contained a minor amount of crystalline impurity but the major phase, denominated AlPO₄-18, had an X-ray powder diffraction pattern characterized by the following data, wherein "I" is the intensity and "d" the interplanar spacing:

| 2θ | d | 100 × I/Io |
|---|---|---|
| 9.60 | 9.21 | 100 |
| 10.45 | 8.47 | 8 |
| 11.0 | 8.04 | 9 |
| 13.1 | 6.76 | 6 |
| 14.0 | 6.33 | 8 |
| 14.8 | 5.99 | 10 |
| 15.5 | 5.72 | 27 |
| 16.9 | 5.25 | 61 |
| 17.0 | 5.22 | |
| 17.9 | 4.96 | 20 |
| 19.3 | 4.60 | 17 |
| 19.5 | 4.55 | |
| 20.15 | 4.41 | 35 |
| 20.95 | 4.24 | 45 |
| 22.1 | 4.02 | 17 |
| 22.3 | 3.99 | |
| 23.3 | 3.82 | 5 |
| 23.85 | 3.73 | 6 |
| 24.4 | 3.65 | 14 |
| 24.9 | 3.58 | 9 |
| 25.4 | 3.51 | 6 |
| 26.1 | 3.41 | 13 |
| 26.45 | 3.37 | 12 |
| 26.8 | 3.33 | |
| 28.0 | 3.19 | 16 |
| 29.0 | 3.08 | 7 |
| 30.0 | 2.98 | 20 |
| 30.75 | 2.91 | 14 |
| 31.3 | 2.86 | 14 |
| 31.8 | 2.81 | 24 |
| 32.4 | 2.76 | |
| 33.4 | 2.68 | 6 |
| 34.5 | 2.60 | 3 |
| 35.8 | 2.51 | 3 |
| 36.2 | 2.48 | |
| 38.2 | 2.36 | 2 |
| 40.2 | 2.24 | 1 |
| 41.7 | 2.17 | 3 |
| 42.9 | 2.11 | 5 |
| 47.8 | 1.90 | 3 |
| 48.6 | 1.87 | 2 |
| 49.6 | 1.84 | 4 |
| 51.0 | 1.79 | 4 |
| 52.0 | 1.76 | 2 |
| 54.2 | 1.69 | 4 |
| 55.1 | 1.67 | 2 |

The species AlPO₄-18 as herein referred to is a crystalline metallophosphate whose essential framework structure has a chemical composition, expressed in terms of molar ratios of oxides, is Al₂O₃:1.0±0.2 P₂O₅ and having a characteristic X-ray powder diffraction pattern which contains at least the d-spacings set forth in Table 17 below:

TABLE 17

| 2θ | d | 100 × I/Io |
|---|---|---|
| 9.60–9.65 | 9.21–9. | 100 |
| 15.5–15.55 | 5.72–5.70 | 27–34 |
| 16.9–17.1 | 5.25–5.19 | 61–70 |
| 17.9 | 4.96 | 20–25 |
| 20.15–20.25 | 4.41–4.39 | 35–43 |
| 20.95–21.05 | 4.24–4.22 | 45–52 |
| 30.0–30.1 | 2.98–2.97 | 20–25 |
| 31.8–32.5 | 2.81–2.75 | 24–27 |

All of the AlPO₄-18 compositions for which the X-ray powder diffraction data has presently been obtained have patterns that are within the generalized pattern of Table 18 below:

TABLE 18

| 2θ | d | 100 × I/Io |
|---|---|---|
| 9.60–9.65 | 9.21–9.17 | 100 |
| 10.45–10.50 | 8.47–8.42 | 8 |
| 11.0–11.05 | 8.04–8.01 | 9–12 |
| 13.1–13.2 | 6.76–6.71 | 6–7 |
| 14.0 | 6.33 | 8 |
| 14.8–14.85 | 5.99–5.97 | 10–11 |
| 15.5–15.55 | 5.72–5.70 | 27–34 |
| 16.9–17.1 | 5.25–5.19 | 61–70 |
| 17.9 | 4.96 | 20–25 |
| 19.35–19.6 | 4.59–4.53 | 8–17 |
| 20.15–20.25 | 4.41–4.39 | 35–43 |
| 20.95–21.05 | 4.27–4.22 | 45–52 |
| 22.1–22.3 | 4.02–3.99 | 17–19 |
| 23.3–23.4 | 3.82–3.80 | 5–7 |
| 23.85–24.0 | 3.73–3.71 | 6–8 |
| 24.4–24.5 | 3.65–3.63 | 14 |
| 24.9–25.0 | 3.58–3.56 | 9–11 |
| 25.4–25.55 | 3.51–3.49 | 6–7 |
| 26.1–26.2 | 3.41–3.40 | 13–15 |
| 26.45–26.9 | 3.37–3.31 | 12 |
| 28.0–28.2 | 3.19–3.16 | 16–17 |
| 30.0–30.1 | 3.98–3.97 | 20–25 |
| 30.75–30.9 | 2.91–2.87 | 14–17 |
| 31.3–31.4 | 2.86–2.85 | 14–15 |
| 31.8–32.5 | 2.81–2.75 | 24–27 |
| 33.3–33.55 | 2.69–2.67 | 6 |
| 34.5–34.6 | 2.60–2.59 | 3–4 |
| 35.8–36.2 | 2.51–2.48 | 3–4 |
| 40.0–40.2 | 2.25–2.24 | 1–2 |
| 41.7–41.8 | 2.17–2.16 | 2–3 |
| 42.9–43.0 | 2.11–2.10 | 5 |
| 47.8 | 1.90 | 3–4 |
| 49.6 | 1.84 | 4–5 |
| 51.0 | 1.79 | 4–7 |
| 52.0 | 1.76 | 2–4 |
| 54.2–54.4 | 1.69–1.69 | 3–4 |

(b) A portion of the solid crystalline product obtained from a similar preparation and exhibiting an X-ray powder diffraction pattern essentially identical to that of part (a) was calcined stepwise in 100° increments from 100° to 600° C., being held at each temperature for one hour before the next increment. The calcined product had an X-ray powder diffraction pattern characterized by the following data:

| 2θ | d | 100 × I/Io |
|---|---|---|
| 9.5 | 9.31 | 100 |
| 10.0 | 8.85 | sh |
| 10.4 | 8.51 | sh |
| 10.6 | 8.35 | 14 |
| 11.3 | 7.83 | 4 |
| 12.95 | 6.83 | 9 |
| 13.5 | 6.56 | 8 |
| 14.5 | 6.11 | 4 |
| 16.1 | 5.50 | 11 |
| 17.0 | 5.22 | 18 |
| 17.2 | 5.16 | 17 |
| 19.1 | 4.65 | 5 |
| 19.7 | 4.51 | 7 |
| 20.0 | 4.44 | 6 |
| 20.7 | 4.29 | 12 |
| 21.3 | 4.17 | 15 |
| 21.9 | 4.06 | 5 |
| 22.5 | 3.95 | 8 |
| 22.9 | 3.88 | 9 |
| 23.9 | 3.72 | 12 |
| 24.3 | 3.66 | sh |
| 24.9 | 3.58 | 3 |
| 25.2 | 3.53 | 3 |
| 25.7 | 3.47 | sh |
| 26.0 | 3.43 | 8 |
| 26.3 | 3.39 | 7 |
| 27.1 | 3.29 | 4 |
| 27.8 | 3.21 | 7 |
| 29.1 | 3.07 | 7 |
| 30.0 | 2.98 | 8 |
| 30.4 | 2.94 | sh |
| 31.0 | 2.88 | 13 |
| 31.6 | 2.83 | 5 |
| 32.2 | 2.78 | 7 |
| 32.6 | 2.75 | sh |
| 33.0 | 2.71 | sh |
| 33.7 | 2.66 | 4 |
| 34.7 | 2.59 | 3 |
| 37.0 | 2.43 | 2 |
| 38.8 | 2.32 | 2 |
| 43.2 | 2.09 | 2 |
| 49.0 | 1.86 | 4 |
| 55.2 | 1.66 | 3 |
| 55.8 | 1.65 | 2 |

EXAMPLE 47 Preparation of AlPO$_4$-20

(a) A reaction mixture was prepared by combining 23.1 grams of 85% orthophosphoric acid (H$_2$PO$_4$) and 34.6 grams of water, to which was added 13.8 grams of a hydrated aluminum oxide (a pseudo-boehmite phase, 74.2 wt.% Al$_2$O$_3$, 25.8 wt. % H$_2$O), and stirred until homogeneous. To this mixture was added 36.2 grams of tetramethylammonium hydroxide pentahydrate (TMAOH.5H$_2$O) dissolved in 50 grams of H$_2$O and the mixture stirred until homogeneous. The composition of the final reaction mixture in molar oxide ratios was:

0.5 (TMA)$_2$O:Al$_2$O$_3$:P$_2$O$_5$:43H$_2$O

The reaction mixture was sealed in a stainless steel pressure vessel lined with polytetrafluoroethylene and heated in an oven at 150° C. at autogenous pressure for 71 hours. The solid reaction product was recovered by repeated centrifugation and washing with water, and dried in air at room temperature. Chemical analysis of the product showed 6.0 wt.% C, 1.76 wt.% N, 32.7 wt.% Al$_2$O$_3$, 44.8 wt.% P$_2$O$_5$, 22.8 wt.% LOI, giving a product composition in molar oxide ratios of:

0.20 (TMA)$_2$O:1.00 Al$_2$O$_3$:0.98 P$_2$O$_5$:2.17H$_2$O

The AlPO$_4$-20 product contained a minor amount of crystalline impurity, but the major phase had an X-ray powder diffraction pattern characterized by the following data, wherein "I" is the intensity and "d" the interplanar spacing:

| 2θ | d | 100 × I/Io |
|---|---|---|
| 14.0 | 6.326 | 51 |
| 19.9 | 4.462 | 44 |
| 22.3 | 3.986 | 16 |
| 24.5 | 3.633 | 100 |
| 28.2 | 3.164 | 25 |
| 31.6 | 2.831 | 18 |
| 34.7 | 2.585 | 18 |
| 40.3 | 2.238 | 4 |
| 43.1 | 2.099 | 5 |
| 47.8 | 1.903 | 4 |
| 52.2 | 1.752 | 10 |

(b) A portion of the solid crystalline product obtained from a similar preparation and exhibiting an X-ray powder diffraction pattern essentially identical to that of part (a) was calcined in air at about 100° C. for 1 hour, 200° C. for 1 hour, 400° C. for 1 hour and finally at 620° C. for 1 hour. The calcined product had an X-ray powder diffraction pattern characterized by the following data:

| 2θ | d | 100 × I/Io |
|---|---|---|
| 14.3 | 6.19 | 100 |
| 20.3 | 4.37 | 27 |
| 22.7 | 3.92 | 9 |
| 24.8 | 3.59 | 57 |
| 28.4 | 3.14 | 20 |
| 32.1 | 2.79 | 19 |
| 35.1 | 2.56 | 13 |
| 40.9 | 2.21 | 4 |
| 52.7 | 1.74 | 6 |

AlPO₄-20 appears to be a structural analogue of the alumino-silicate sodalite.

EXAMPLE 48. Preparation of AlPO₄-20

A reaction mixture was prepared by combining 57.6 grams of 85% orthophosphoric acid (H₃PO₄) and 90.5 grams of water, to which was added 37.8 grams of the same hydrated aluminum oxide as in Example 47 and stirred until homogeneous. To this mixture was added 36.2 grams of tetramethylammonium hydroxide pentahydrate (TMAOH.5H₂O) and 2.0 grams of sodium hydroxide dissolved in 50 grams of H₂O, and the mixture stirred until homogeneous. The composition of the final reaction mixture in molar oxide ratios was:

0.1 Na₂O:0.4(TMA)₂O:1.1Al₂O₃:P₂O₅:43 H₂O

The reaction mixture was placed in a sealed stainless steel pressure vessel lined with an inert plastic material and heated in an oven at 150° C. at autogenous pressure for 72 hours. The solid reaction product was recovered by centrifuging and washing with water, and dried in air at 110° C. A portion of the solids was subjected to X-ray analysis. The AlPO₄-20 product had an X-ray powder diffraction pattern essentially identical to that of the uncalcined product in example 47 (a).

EXAMPLE 49. Preparation of AlPO₄-20

A reaction mixture was prepared by combining 92.1 grams of 85% orthophosphoric acid (H₃PO₄) and 220.9 grams of water, to which was added 55.0 grams of a hydrated aluminum oxide (Catapal SB, a pseudo-boehmite phase, 74.2 wt.% Al₂O₃, 25.8 wt.% H₂O), and stirred until homogeneous. To this mixture was added 72.5 grams of tetramethylammonium hydroxide pentahydrate (TMAOH.5 H₂O) dissolved in 50 grams H₂O and the mixture stirred until homogeneous. To this mixture 13.0 grams of NaA zeolite were added and the mixture homogenized. Exclusive of the NaA zeolite, the composition of the final reaction mixture in molar oxide ratios was:

0.5 (TMA)₂O:Al₂O₃:P₂O₅:50 H₂O

The reaction mixture was placed in a stainless steel pressure vessel having an inert plastic lining and heated in an oven at 125° C. at autogenous pressure for 53 hours. The solid reaction product was recovered by centrifuging and washing with water, and dried in air at 110° C. The AlPO₄-20 product had an X-ray powder diffraction pattern essentially identical to that of the product in Example 47 (a).

The species AlPO₄-20 as herein referred to is a crystalline metallophosphate whose essential framework structure has a chemical composition, expressed in terms of molar ratios of oxides, is Al₂O₃: 1.0±0.2 P₂O₅ and having a characteristic X-ray powder diffraction pattern which contains at least the d-spacings set forth in Table 19 below:

TABLE 19

| 2θ | d | 100 × I/Io |
|---|---|---|
| 13.9–14.1 | 6.37–6.28 | 40–55 |
| 19.8–20.0 | 4.48–4.44 | 40–48 |
| 24.3–24.5 | 3.66–3.63 | 100 |
| 28.2–28.3 | 3.16–3.15 | 12–25 |
| 31.4–31.7 | 2.85–2.82 | 11–18 |
| 34.6–34.8 | 2.59–2.58 | 15–18 |

All of the AlPO₄-20 compositions for which the X-ray powder diffraction data has presently been obtained have patterns that are within the generalized pattern of Table 20 below:

TABLE 20

| 2θ | d | 100 × I/Io |
|---|---|---|
| 13.9–14.1 | 6.37–6.28 | 40–55 |
| 19.8–20.0 | 4.48–4.44 | 40–48 |
| 22.2–22.4 | 4.00–3.97 | 5–16 |
| 24.3–24.5 | 3.66–3.63 | 100 |
| 28.2–28.3 | 3.16–3.15 | 12–25 |
| 31.4–31.7 | 2.85–2.82 | 11–18 |
| 34.6–34.8 | 2.59–2.58 | 15–18 |
| 40.2–40.5 | 2.24–2.23 | 4–5 |
| 42.7–43.1 | 2.12–2.01 | 5–8 |
| 47.5–47.8 | 1.91–1.90 | 4–7 |
| 51.9–52.2 | 1.76–1.75 | 10–11 |

EXAMPLE 50. Preparation of AlPO₄-22

(a) A reaction mixture was prepared by combining 57.7 grams of 85% orthophosphoric acid (H₃PO₄) and 80.4 grams of water, to which was added 34.4 grams of a hydrated aluminum oxide (a pseudo-boehmite phase, 74.2 wt.% Al₂O₃, 25.8 wt.% H₂O), and stirred until homogeneous. To this mixture was added 110.6 grams of an aqueous solution of 68.2 wt.% N,N'-dimethyl-1,4-diazabicyclo(2,2,2) octane dihydroxide (DDO), and the mixture stirred until homogeneous. The composition of the final reaction mixture in molar oxide ratios was:

1.7 DDO:Al₂O₃:P₂O₅:40 H₂O

The reaction mixture was sealed in a lined stainless steel pressure vessel and heated in an oven at 200° C. at autogeneous pressure for 72 hours. The solid reaction product was recovered by filtration, washed with water, and dried in air at 110° C. Chemical analysis showed 9.6 wt.% C, 2.9 wt.% N, 33.2 wt.% Al₂O₃, 47.6 wt.% P₂O₅, 19.4 wt.% LOI, giving a product composition in molar oxide ratios of:

0.31 DDO:1.0 Al₂O₃:1.03 P₂O₅:0.31 H₂O

The above product, denominated AlPO₄-22, had an X-ray powder diffraction pattern characterized by the following data, wherein "I" is the intensity and "d" the interplanar spacing:

| 2θ | d | 100 × I/Io |
|---|---|---|
| 8.55 | 10.34 | 25 |
| 9.0 | 9.83 | 2 (sh) |
| 9.1 | 9.72 | 57 |
| 11.4 | 7.76 | 1 |
| 12.7 | 6.97 | (sh) |
| 13.0 | 6.81 | 9 |
| 14.6 | 6.07 | 4 |
| 15.6 | 5.68 | 6 |
| 17.3 | 5.13 | 26 |
| 18.5 | 4.80 | 100 |
| 20.65 | 4.30 | 43 |
| 21.4 | 4.15 | 1 (sh) |
| 21.75 | 4.08 | 19 |
| 22.6 | 3.93 | 6 |
| 23.7 | 3.75 | 22 |

| 2θ | d | 100 × I/Io |
|---|---|---|
| 23.85 | 3.7 | 23 |
| 24.2 | 3.68 | 8 |
| 24.8 | 3.59 | 24 |
| 26.2 | 3.40 | 36 |
| 27.0 | 3.30 | (sh) |
| 27.3 | 3.27 | 20 |
| 27.8 | 3.21 | 8 |
| 28.6 | 3.12 | 10 |
| 29.3 | 3.05 | 30 |
| 30.1 | 2.969 | 8 |
| 31.55 | 2.835 | 16 |
| 32.2 | 2.780 | 2 |
| 33.0 | 2.714 | 2 |
| 33.2 | 2.698 | 2 |
| 34.15 | 2.625 | 2 |
| 34.9 | 2.571 | 11 |
| 35.55 | 2.525 | 5 |
| 37.4 | 2.404 | (sh) |
| 37.6 | 2.392 | 9 |
| 39.1 | 2.304 | 1 |
| 39.25 | 2.295 | 1 |
| 39.75 | 2.268 | 2 |
| 40.35 | 2.235 | 4 |
| 41.2 | 2.191 | 2 |
| 42.1 | 2.146 | 2 |
| 43.7 | 2.071 | 1 |
| 44.3 | 2.045 | 4 |
| 44.7 | 2.027 | 2 |
| 45.2 | 2.006 | 4 |
| 46.4 | 1.957 | 1 |
| 47.0 | 1.933 | 2 |
| 48.4 (sh) | 1.881 | 4 |
| 48.75 | 1.868 | 13 |
| 49.7 | 1.834 | 5 |
| 50.2 | 1.817 | 2 |
| 51.4 | 1.778 | <1 |
| 53.2 | 1.722 | 3 |
| 54.0 | 1.698 | 5 |
| 54.4 | 1.687 | 2 |

(sh = shoulder)

(b) A portion of the solid crystalline product obtained above was calcined in air at about 600° C. for 2 hours. The calcined AlPO$_4$-22 had an X-ray powder diffraction pattern characterized by the following data:

| 2θ | d | 100 × I/Io |
|---|---|---|
| 8.6 | 10.28 | (sh) |
| 9.15 | 9.65 | 100 |
| 12.6 | 7.03 | |
| 12.9 | 6.86 | 42 |
| 13.0 | 6.81 | |
| 14.4 | 6.15 | |
| | | 21 |
| 14.7 | 6.03 | |
| 17.3 | 5.13 | 50 |
| 18.5 | 4.80 | 92 |
| 20.4 | 4.35 | 64 |
| 21.55 | 4.12 | 23 |
| 22.5 | 3.95 | 11 |
| 23.9 | 3.72 | 34 |
| 24.8 | 3.59 | 18 |
| 25.9 | 3.44 | 32 |
| 26.1 | 3.41 | (sh) |
| 27.3 | 3.27 | 24 |
| 27.5 | 3.24 | (sh) |
| 28.4 | 3.14 | 12 |
| 29.1 | 3.07 | 31 |
| 31.2 | 2.867 | |
| | | 19 |
| 31.4 | 2.849 | |
| 32.9 | 2.722 | 4 |
| 34.55 | 2.596 | 15 |
| 34.9 | 2.571 | 14 |
| 35.5 | 2.529 | 5 |
| 37.3 | 2.411 | 3 |
| 39.6 | 2.275 | 1 |
| 40.8 | 2.212 | 3 |
| 41.5 | 2.176 | 1 |
| 44.4 | 2.040 | 4 |
| 44.9 | 2.019 | 2 |
| 46.7 | 1.945 | 3 |
| 47.2 | 1.926 | 2 |
| 47.8 | 1.903 | 3 |
| 48.2 | 1.888 | 3 |
| 49.0 | 1.859 | 2 |
| 52.7 | 1.737 | 2 |
| 53.4 | 1.716 | 4 |

The species AlPO$_4$-22 as herein referred to is a crystalline metallophosphate whose essential framework structure has a chemical composition, expressed in terms of molar ratios of oxides, is:

Al$_2$O$_3$: 1.0±0.2 P$_2$O$_5$ and having a characteristic X-ray powder diffraction pattern which contains at least the d-spacings set forth in Table 21 below:

TABLE 21

| 2θ | d | 100 × I/Io |
|---|---|---|
| 9.1–9.15 | 9.72–9.66 | 57–100 |
| 18.45–18.5 | 4.81–4.80 | 66–100 |
| 20.55–20.65 | 4.32–4.30 | 43–70 |
| 26.1–26.2 | 3.41–3.40 | 36–44 |
| 29.3 | 3.05 | 30–32 |
| 31.55 | 2.835 | 16–29 |

All of the AlPO$_4$-22 compositions for which the X-ray powder diffraction data has presently been obtained have patterns that are within the generalized pattern of Table 22 below:

TABLE 22

| 2θ | d | 100 × I/Io |
|---|---|---|
| 8.55 | 10.34 | 15–25 |
| 9.0 | 9.83 | (sh) |
| 9.1–9.15 | 9.72–9.66 | 57–100 |
| 11.4 | 7.76 | 0–1 |
| 12.7 | 6.97 | (sh) |
| 12.95–13.0 | 6.83–6.81 | 9–14 |
| 14.5–14.6 | 6.11–6.07 | 3–5 |
| 15.55–15.6 | 5.70–5.68 | 4–6 |
| 17.25–17.3 | 5.14–5.13 | 22–26 |
| 18.45–18.5 | 4.81–4.80 | 66–100 |
| 20.55–20.65 | 4.32–4.30 | 43–70 |
| 21.65–21.75 | 4.10–4.09 | 12–19 |
| 22.6 | 3.93 | 6–7 |
| 23.6–23.7 | 3.77–3.75 | 22 |
| 23.8–23.85 | 3.74–3.73 | 18–23 |
| 24.2 | 3.68 | 8–14 |
| 24.7–24.8 | 3.60–3.59 | 10–24 |
| 26.1–26.2 | 3.41–3.40 | 36–44 |
| 27.0 | 3.30 | (sh) |
| 27.2–27.3 | 3.28–3.27 | 17–20 |
| 27.7–27.8 | 3.22–3.21 | 8–23 |
| 28.6 | 3.12 | 10–14 |
| 29.3 | 3.05 | 30–32 |
| 30.1 | 2.969 | 6–8 |
| 31.55 | 2.835 | 16–29 |
| 32.2 | 2.780 | 0–2 |
| 32.9–33.0 | 2.722–2.714 | 2–3 |
| 33.2–33.3 | 2.698–2.691 | 2–3 |
| 34.1–34.15 | 2.629–2.625 | 2–3 |
| 34.9 | 2.571 | 5–11 |
| 35.55 | 2.525 | 5–8 |
| 37.4 | 2.404 | (sh) |
| 37.5–37.6 | 2.398–2.392 | 6–9 |
| 39.0–39.25 | 2.309–2.295 | 1–2 |
| 39.75 | 2.267 | 0–2 |
| 40.30–40.35 | 2.238–2.235 | 2–3 |

TABLE 22-continued

| 2θ | d | 100 × I/Io |
|---|---|---|
| 41.0–41.2 | 2.201–2.191 | 1–2 |
| 41.9–42.1 | 2.156–2.146 | 2–3 |
| 43.7 | 2.071 | 1–5 |
| 44.2–44.3 | 2.049–2.045 | 3–4 |
| 44.7–44.9 | 2.027–2.019 | 1–2 |
| 45.2–45.3 | 2.006–2.002 | <1–4 |
| 46.2–46.4 | 1.965–1.957 | <1–1 |
| 46.8–47.0 | 1.941–1.933 | <1–2 |
| 48.1–48.4 | 1.892–1.881 | (sh)–6 |
| 48.6–48.75 | 1.873–1.868 | 13–19 |
| 49.6–49.7 | 1.838–1.834 | 4–5 |
| 50.1–50.2 | 1.821–1.817 | 1–2 |
| 51.4 | 1.778 | <1 |
| 53.0–53.2 | 1.728–1.722 | 2–3 |
| 53.8–54.0 | 1.704–1.698 | 5–6 |
| 54.3–54.4 | 1.689–1.687 | 2 |

EXAMPLE 51. Preparation of AlPO₄-25

The crystalline metallophosphate denominated AlPO₄-25 is preferably prepared by the thermally induced structural conversion of a less stable crystalline intermediate which is synthesized by hydrothermal crystallization from a reaction gel in a manner similar to that employed to obtain most of the AlPO₄-n species of the present invention. This intermediate, identified as AlPO₄-21 is readily synthesized using a considerable variety of organic templating agents which are removed from the structure during calcination to produce the stable AlPO₄-25.

(a) Preparation of AlPO₄-21.

A reaction mixture was prepared by combining 7.7 grams of 85% orthophosphoric acid ($H_3PO_4$) and 25.9 grams of water, to which was added 4.6 grams of a pseudo-boehmite phase (74.2 wt.% $Al_2O_3$, 25.8 wt.% $H_2O$), and stirred until homogeneous. To this mixture was added 2.4 grams of $(CH_2)_4$:NH, (pyrrolidine), and the mixture stirred until homogeneous. The composition of the final reaction mixture in molar oxide ratios was:

1.0 $(CH_2)_4$:NH:$Al_2O_3$:$P_2O_5$:40 $H_2O$

The reaction mixture was sealed in a stainless steel pressure vessel lined with polytetrafluoroethylene and heated in an oven at 150° C. at autogenous pressure for 150 hours. The solid reaction product was recovered by filtration, washed with water, and dried in air at 110° C. Chemical analysis of the product showed 10.2 wt.-% C, 3.2 wt.-% N, 32.1 wt.% $Al_2O_3$, 47.1 wt.% $P_2O_5$, 19.8 wt.% LOI, giving a product composition in molar oxide ratios of:

0.67 $(CH_2)_4NH$:1.00 $Al_2O_3$: 1.05 $P_2O_5$: 0.83 $H_2O$ The product was designated AlPO₄-21, and had an X-ray powder diffraction pattern characterized by the following data, wherein "I" is the intensity and "d" the interplanar spacing:

| 2θ | d | 100 × I/Io |
|---|---|---|
| 10.0 | 8.845 | 51 |
| 10.5 | 8.425 | 7 |
| 11.3 | 7.830 | 14 |
| 11.8 | 7.500 | 13 |
| 12.2 | 7.255 | 36 |
| 13.2 | 6.707 | 6 |
| 14.2 | 6.237 | 36 |
| 14.6 | 6.067 | 27 |
| 15.9 | 5.574 | 31 |
| 16.8 | 5.277 | 6 |
| 18.5 | 4.796 | 4 |
| 19.6 | 4.529 | 11 |
| 20.4 | 4.353 | 25 |
| 21.1 | 4.210 | 25 |
| 21.3 | 4.171 | 30 |
| 22.6 | 3.934 | 97 |
| 22.8 | 3.900 | 88 |
| 23.7 | 3.754 | 23 |
| 25.1 | 3.548 | 100 |
| 25.8 | 3.453 | 6 |
| 26.2 | 3.401 | 19 |
| 26.6 | 3.351 | 53 |
| 27.6 | 3.232 | 47 |
| 28.2 | 3.164 | 21 |
| 29.0 | 3.079 | 11 |
| 29.4 | 3.038 | 3 |
| 30.6 | 2.921 | 5 |
| 31.0 | 2.885 | 8 |
| 32.0 | 2.797 | 35 |
| 32.6 | 2.747 | 23 |
| 32.9 | 2.722 | 38 |
| 34.0 | 2.637 | 15 |
| 35.2 | 2.550 | 2 |
| 35.9 | 2.501 | 6 |
| 37.2 | 2.417 | 12 |
| 37.8 | 2.380 | 3 |
| 38.8 | 2.321 | 5 |
| 40.2 | 2.243 | 7 |
| 44.4 | 2.040 | 7 |
| 47.6 | 1.910 | 8 |
| 50.8 | 1.797 | 7 |
| 52.0 | 1.759 | 9 |
| 52.6 | 1.740 | 11 |
| 53.2 | 1.722 | 8 |
| 54.0 | 1.698 | 7 |

(b) A procedure similar to that in part (a) above was followed except where indicated in Table E. A portion of the solid product from each reaction was subjected to X-ray analysis and in each case a phase characterized by an X-ray powder diffraction pattern essentially the same as that in part (a) was observed alone or in admixture.

TABLE E

| Example # | Organic Used (R) | Reaction Mixture Composition | | | | Digestion Time (Hrs.) | Temp. (°C.) |
|---|---|---|---|---|---|---|---|
| | | R | $Al_2O_3$ | $P_2O_5$ | $H_2O$ | | |
| (b)1 | $(CH_3)_3N$ Trimethylamine | 1 | 1 | 1 | 50 | 94 | 150 |
| (b)2 | $(CH_2)_4$:NH Pyrrolidine | 1 | 1 | 1 | 50 | 166 | 150 |
| (b)3 | $C_6H_{14}N_2$ 1,4-Dimethyl Piperazine | 1 | 1 | 1 | 50 | 168 | 200 |
| b(4) | $C_{11}H_{26}N_2$ 3-(di-n-butylamino)-Propylamine | 1 | 1 | 1 | 40 | 168 | 200 |
| (b)5 | $C_7H_{18}N_2$ N,N,N',N'-tetramethyl-1,3-propanediamine | 1 | 1 | 1 | 40 | 168 | 200 |
| (b)6 | $C_4H_{11}NO$ | 1 | 1 | 1 | 40 | 336 | 200 |

TABLE E-continued

| Example # | Organic Used (R) | Reaction Mixture Composition | | | | Digestion Time (Hrs.) | Temp. (°C.) |
|---|---|---|---|---|---|---|---|
| | | R | $Al_2O_3$ | $P_2O_5$ | $H_2O$ | | |
| (b)7 | N,N-dimethyl-ethanolamine n-$C_3H_7NH_2$ n-Propylamine | 1 | 1 | 1 | 50 | 334 | 200 |
| (b)8 | $C_4H_{16}N_2$ N,N,N',N'-tetramethyl-ethylenediamine | 1 | 1 | 1 | 50 | 168 | 200 |
| (b)9 | $C_3H_6NO$ N-Methyl-ethanolamine | 1 | 1 | 1 | 50 | 168 | 200 |

Preparation of $AlPO_4$-25

(c) A portion of the $AlPO_4$-21 crystalline product obtained in part (a) was calcined in air at about 600° C. for 2 hours. The calcined product had an X-ray powder diffraction pattern quite different from the starting $AlPO_4$-21 and is a new and novel microporous aluminophosphate species denominated $AlPO_4$-25. The X-ray pattern of this species is characterized by the following data:

| 1θ | d | 100 × I/Io |
|---|---|---|
| 7.6 | 11.632 | 3 |
| 9.6 | 9.213 | 83 |
| 10.6 | 8.346 | 1 |
| 11.8 | 7.500 | 14 |
| 12.6 | 7.025 | 3 |
| 15.2 | 5.829 | 100 |
| 19.1 | 4.647 | 71 |
| 21.3 | 4.171 | 84 |
| 22.7 | 3.917 | 17 |
| 23.6 | 3.770 | 8 |
| 24.6 | 3.619 | 6 |
| 25.5 | 3.490 | 43 |
| 26.1 | 3.414 | 14 |
| 28.6 | 3.121 | 10 |
| 29.9 | 2.988 | 3 |
| 31.0 | 2.885 | 23 |
| 33.2 | 2.698 | 8 |
| 35.7 | 2.515 | 7 |
| 37.4 | 2.404 | 8 |
| 37.9 | 2.374 | 8 |
| 43.2 | 2.094 | 3 |
| 53.3 | 1.719 | 3 |

(d) Five $AlPO_4$-21 samples crystallized in parts (b)1, (b)3, (b)5, (b)7 and (b)9, respectively, were calcined at 500°-600° C. in air and found to convert to the crystal structure characteristic of $AlPO_4$-25. It is believed all $AlPO_4$-21 compositions can be converted to $AlPO_4$-25 in a similar manner.

The species $AlPO_4$-25 as herein referred to is a crystalline metallophosphate whose essential framework structure has a chemical composition, expressed in terms of molar oxides, is $Al_2O_3$:1.0±0.2 $P_2O_5$ and having a characteristic X-ray powder diffraction pattern which contains at least the d-spacings set forth in Table 23 below:

TABLE 23

| 2θ | d | 100 × I/Io |
|---|---|---|
| 9.4 | 9.41 | 32–96 |
| 15.0 | 5.91 | 35–76 |
| 18.8–18.9 | 4.72–4.70 | 35–100 |
| 21.1 | 4.21 | 28–100 |
| 22.5 | 3.95 | 16–32 |
| 25.3 | 3.52 | 14–37 |

TABLE 23-continued

| 2θ | d | 100 × I/Io |
|---|---|---|
| 30.8–30.9 | 2.90–2.89 | 20–31 |

EXAMPLE 52 Preparation of $AlPO_4$-26.

A solution of 200 grams 1,4-dibromobutane in 500° cc of a 4:1 volume mixture of dimethylformamide:methanol (DMF/MeOH) was prepared and cooled to 0° in an ice/water bath. To this was added a solution of 159.4 grams N,N,N',N'-tetramethyl-1,6-hexanediamine in 500 cc 4:1 DMF/MeOH. This mixture was stirred for three days, gradually warming to ambient temperature. The product mass was slurried in diethylether, filtered, washed with ether and dried in air at ambient temperature. The product was a polymeric quaternary ammonium salt, $[(C_{14}H_{32}N_2)Br_2]_x$:

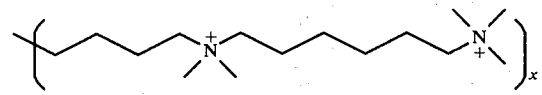

In order to obtain the hydroxide form, 200 grams of the above polymer was dissolved in 800 grams of $H_2O$ and added dropwise over 6 hours to a stirred suspension of 131.4 grams $Ag_2O$ in 1000 grams $H_2O$. The resulting mixture was stirred overnight and filtered. Chemical analysis of the filtrate showed 1.9 wt.% C, 0.32 wt.% N, and 0.014 wt.% Br, corresponding to an aqueous solution containing 3.0 wt.% of the polymer $[(C_{14}H_{32}N_2)(OH)_2]_x$. The concentration of the polymer in a portion of the filtrate was increased to 12.9 wt.% by removing $H_2O$ at reduced pressure.

A reaction mixture was prepared by combining 101.6 grams of the above aqueous solution containing 12.9 wt.% of the polymeric quaternary ammonium hydroxide with 6.9 grams of a hydrated aluminum oxide (a pseudoboehmite phase, 74.2 wt.% $Al_2O_3$, 25.8 wt.% $H_2O$). This mixture was stirred until homogeneous. To this mixture was added 11.5 grams 85 wt.% orthophosphoric acid and the mixture stirred until homogeneous. The composition of the final reaction mixture in molar oxide ratios was:

1.0$(C_{14}H_{32}N_2)(OH)_2$:$Al_2O_3$:$P_2O_5$:105$H_2O$

The reaction mixture was placed in a sealed stainless steel pressure vessel having an inert liner and heated in an oven at 200° C. at autogenous pressure for 24 hours. The solid reaction product was recovered by filtration, washed with water, and dried in air at 110° C. The resulting $AlPO_4$-26 product had an X-ray powder diffraction pattern characterized by the following data, wherein "I" is the intensity and "d" the interplanar spacing:

TABLE 24

| 2θ | d | 100 × I/Io |
|---|---|---|
| 8.35 | 10.59 | 100 |
| 9.85 | 8.98 | 14 |
| 10.2 | 8.67 | (sh) |
| 10.55 | 8.38 | 68 |
| 11.8 | 7.50 | 1 |
| 13.5 | 6.56 | 8 |
| 14.5 | 6.11 | 6 |
| 15.45 | 5.73 | 3 |
| 16.8 | 5.28 | 10 |
| 17.65 | 5.02 | 15 |
| 18.05 | 4.91 | 18 |
| 19.0 | 4.67 | 1 |
| 19.9 | 4.46 | 11 |
| 20.3 | 4.37 | 1 |
| 21.65 | 4.10 | 4 |
| 22.25 | 3.99 | 31 |
| 23.05 | 3.86 | } 74 |
| 22.9 | 3.88 |  |
| 24.7 | 3.60 | 6 |
| 25.25 | 3.527 | 10 |
| 25.85 | 3.446 | 2 |
| 27.2 | 3.278 | 10 |
| 27.45 | 3.249 | 6 |
| 27.95 | 3.192 | 6 |
| 29.2 | 3.058 | 4 |
| 29.7 | 3.008 | 1 |
| 30.45 | 3.036 | 9 |
| 30.9 | 2.8938 | } 12 |
| 31.1 | 2.875 |  |
| 31.6 | 2.83 | 2 |
| 32.25 | 2.776 | 8 |
| 32.7 | 2.739 | 1 |
| 33.8 | 2.652 | 1 |
| 34.3 | 2.614 | 6 |
| 35.0 | 2.564 | 1 |
| 35.4 | 2.536 | 1 |
| 36.15 | 2.485 | <1 |
| 36.4 | 2.468 | <1 |
| 37.45 | 2.401 | 2 |
| 38.6 | 2.332 | <1 |
| 39.0 | 2.309 | <1 |
| 39.4 | 2.287 | 1 |
| 40.0 | 2.254 | <1 |
| 40.5 | 2.227 | 2 |
| 41.3 | 2.186 | 2 |
| 42.4 | 2.132 | 2 |
| 43.1 | 2.099 | 4 |
| 44.2 | 2.049 | <1 |
| 45.7 | 1.985 | <1 |
| 46.1 | 1.969 | 1 |
| 47.8 | 1.903 | 1 |
| 48.15 | 1.890 | 2 |
| 49.1 | 1.855 | 2 |
| 49.7 | 1.834 | <1 |
| 50.7 | 1.801 | <1 |
| 51.4 | 1.778 | 2 |
| 52.5 | 1.743 | 1 |
| 52.9 | 1.731 | <1 |
| 53.7 | 1.707 | 2 |
| 54.4 | 1.687 | 3 |
| 55.2 | 1.664 | 1 |

The species AlPO4-26 as herein referred to is a crystalline metallophosphate whose essential framework structure has a chemical composition, expressed in terms of molar ratios of oxides is:

Al2O3:1±0.2 P2O5 and having an X-ray powder diffraction pattern essentially as set forth in TABLE 24.

EXAMPLE 53 Preparation of AlPO4-28

The crystalline metallophosphate denominated AlPO4-28 is preferably prepared by the thermally induced structural conversion of a less stable crystalline intermediate which is synthesized by hydrothermal crystallization from a reaction gel in a manner similar to that employed to obtain most of the AlPO4-n species of the present invention. This intermediate, identified as AlPO4-23 is readily synthesized using pyrrolidine as the templating agent which is removed from the structure during calcination to produce the stable AlPO4-28.

(a) Preparation of AlPO4-23.

A reaction mixture was prepared by combining 23.1 grams of 85% orthophosphoric acid (H3PO4) and 77.6 grams of water, to which was added 13.8 grams of a hydrated aluminum oxide (a pseudo-boehmite phase, 74.2 wt.% Al2O3, 25.8 wt.% H2O), and stirred until homogeneous. To this mixture was added 7.1 grams of (CH2)4:NH (pyrrolidine), and the mixture stirred until homogeneous. The composition of the final reaction mixture in molar oxide ratios was:

1.0(CH2)4NH:Al2O3:P2O5:50H2O

The reaction mixture was placed in a sealed stainless steel pressure vessel lined with an inert plastic material and heated in an oven at 200° C. at autogenous pressure for 91 hours. The solid reaction product was recovered by filtration, washed with water, and dried in air at 110° C. Chemical analysis showed 9.9 wt.% C, 31. wt.% N, 32.8 wt.% Al2O3, 47.5 wt.% P2O5, 19.3 wt.% LOI, giving a product composition in molar oxide ratios of:

0.64(CH2)4:NH:1.00Al2O3:1.04 P2O4:0.79H2O

The product denominated AlPO4-23 had an X-ray powder diffraction pattern characterized by the following data, wherein "I" is the intensity and "d" the interplanar spacing:

| 2θ | d | 100 × I/Io |
|---|---|---|
| 7.4 | 11.946 | 47 |
| 10.3 | 8.588 | 24 |
| 10.7 | 8.268 | 64 |
| 11.6 | 7.628 | 54 |
| 11.9 | 7.437 | 43 (sh) |
| 13.4 | 6.607 | 4 |
| 14.7 | 6.026 | 4 |
| 15.0 | 5.906 | 6 |
| 16.8 | 5.277 | 6 |
| 19.0 | 4.671 | 21 |
| 20.4 | 4.353 | 28 |
| 21.3 | 4.171 | 100 |
| 23.2 | 3.834 | 65 |
| 24.0 | 3.708 | 9 |
| 24.5 | 3.633 | 6 (sh) |
| 26.2 | 3.401 | 16 |
| 27.2 | 3.278 | 11 |
| 27.8 | 3.209 | 12 |
| 28.6 | 3.121 | 36 |
| 29.6 | 3.018 | 30 |
| 30.8 | 2.903 | 11 |
| 32.2 | 2.780 | 74 |
| 33.8 | 2.652 | 2 |
| 34.9 | 2.571 | 7 |
| 36.2 | 2.481 | 8 |
| 37.4 | 2.404 | 4 |
| 39.2 | 2.298 | 2 |
| 40.7 | 2.217 | 7 |
| 43.3 | 2.090 | 4 |
| 48.2 | 1.888 | 8 |
| 49.8 | 1.831 | 4 |
| 51.8 | 1.765 | 2 |
| 52.8 | 1.734 | 5 |

(b) Preparation of AlPO4-28.

A portion of the AlPO4-23 composition prepared in part (a), supra, was calcined in air at about 600° C. for 2 hours. The calcined product was crystalline but had an X-ray powder diffraction pattern substantially different from the precursor material. It is apparent that the calcination procedure converted the original AlPO₄-23 to a new microporous aluminophosphate species of the present invention, namely AlPO₄-28. The X-ray powder diffraction pattern of the AlPO₄-28 product is as follows:

| $2\theta$ |      | d      | $100 \times I/I_o$ |
|-----------|------|--------|--------------------|
| 7.9       |      | 11.191 | 41                 |
| 9.9       |      | 8.934  | 7                  |
| 12.2      |      | 7.255  | 100                |
| 13.3      | (sh) | 6.657  | 22                 |
| 15.7      |      | 5.644  | 7                  |
| 18.6      |      | 4.770  | 47                 |
| 19.2      | (sh) | 4.623  | 25                 |
| 21.0      |      | 4.230  | 9                  |
| 21.9      |      | 4.058  | 30                 |
| ~23.5     |      | 3.786  | 7                  |
| 25.4      |      | 3.507  | 20                 |
| 26.1      |      | 3.414  | 13                 |
| 27.0      |      | 3.302  | 16                 |
| 29.7      |      | 3.008  | 13                 |
| 30.9      |      | 2.894  | 13                 |
| 32.1      |      | 2.788  | 11                 |
| 35.4      |      | 2.536  | 6                  |
| 36.4      |      | 2.468  | 2                  |

The species AlPO₄-28 as herein referred to is a crystalline metallophosphate whose essential framework structure has a chemical composition, expressed in terms of molar ratios of oxides, is
$Al_2O_3:1.0\pm0.2\ P_2O_5$
and having a characteristic X-ray powder diffraction pattern which contains at least the d-spacings set forth in Table 25 below:

TABLE 25

| $2\theta$ | d     | $100 \times I/I_o$ |
|-----------|-------|--------------------|
| 7.9       | 11.19 | 41                 |
| 12.2      | 7.26  | 100                |
| 18.6      | 4.77  | 47                 |
| 21.9      | 4.06  | 30                 |
| 25.4      | 3.51  | 20                 |
| 27.0      | 3.30  | 16                 |

EXAMPLE 54 Preparation of AlPO₄-31.

(a) A reaction mixture was prepared by dispersing 164.8 grams of a pseudo-boehmite phase (74.2 wt.% $Al_2O_3$, 25.8 wt.% $H_2O$) in 715.2 grams of water, to which was added 276.7 grams of 85% orthophosphoric acid, and stirred until homogeneous. To this mixture was added 121.4 grams of di-(n-propyl) amine ($Pr_2NH$), and the mixture stirred until homogeneous. The composition of the final reaction mixture in molar oxide ratios was:

$1.0Pr_2NH:Al_2O_3:P_2O_5:40H_2O$

The reaction mixture was sealed in a stainless steel pressure vessel lined with polytetrafluoroethylene and heated in an oven at 200° C. at autogeneous pressure for 46 hours. The solid reaction product was recovered by repeated centrifugation and washing with $H_2O$, and dried in air at room temperature. Chemical analysis of the reaction product showed 4.7 wt.% C, 0.85 wt.% N, 37.4 wt.% $Al_2O_3$, 51.6 wt.% $P_2O_5$, 10.3 wt.% LOI, giving a product composition expressed in molar oxide ratios of $0.18Pr_2NH:1.00Al_2O_3:0.99\ P_2O_5:0.56H_2O$ The above product, denominated AlPO₄-31, had an X-ray powder diffraction pattern characterized by the following data, wherein "I" is the intensity and "d" the interplanar spacing:

TABLE 26

| $2\theta$ |    | d     | $100 \times I/I_o$ |
|-----------|----|-------|--------------------|
| 8.5       |    | 10.40 | 85                 |
| 9.5       |    | 9.31  | 12                 |
| 13.35     |    | 6.63  | 6                  |
| 13.8      |    | 6.42  | 2                  |
| 14.8      |    | 5.99  | 2                  |
| 15.7      |    | 5.64  | 6                  |
| 17.1      |    | 5.19  | 7                  |
| 18.3      |    | 4.85  | 7                  |
| 20.0      | sh | 4.44  | —                  |
| 20.3      |    | 4.37  | 48                 |
| 21.1      |    | 4.21  | 28                 |
| 21.8      |    | 4.08  | 26                 |
| 22.6      |    | 3.93  | 100                |
| 23.2      | sh | 3.83  | —                  |
| 24.8      |    | 3.59  | 7                  |
| 25.6      |    | 3.48  | 8                  |
| 27.7      |    | 3.22  | 11                 |
| 28.3      |    | 3.15  | 7                  |
| 29.6      |    | 3.02  | 9                  |
| 29.9      |    | 2.99  | 9                  |
| 31.4      | sh | 2.85  |                    |
| 31.6      |    | 2.83  | 14                 |
| 35.2      |    | 2.55  | 10                 |
| 35.8      |    | 2.51  | 6                  |
| 38.0      |    | 2.37  | 8                  |
| 40.0      |    | 2.25  | 4                  |

(b) A portion of the solid crystalline product obtained above was calcined to a temperature of 1000° C. This calcined material had an X-ray powder diffraction pattern essentially identical to that of part (a).

EXAMPLE 55

(a) Adsorption capacities of AlPO₄-5 (prepared in Ex. 3(b) supra) were measured using a standard McBain-Bakr gravimetric adsorption apparatus. The following data were obtained on a sample activated at 350° C.:

|                              | Kinetic Diameter, Å | Pressure, Torr | Temp., °C | Wt. % Adsorbed |
|------------------------------|---------------------|----------------|-----------|----------------|
| $O_2$                        | 3.46                | 97             | −183      | 12.6           |
| $O_2$                        | 3.46                | 750            | −183      | 17.0           |
| Neopentane                   | 6.2                 | 102            | 24        | 5.5            |
| $(C_4F_9)_3N$(after 4 hours) | 10                  | 0.073          | 24        | 1.2            |
| $H_2O$                       | 2.65                | 4.6            | 24        | 4.6            |
| $H_2O$                       | 2.65                | 18.5           | 23        | 26.4           |

The pore size of the calcined product is greater than 6 and less than 10 Å as shown by adsorption of neopentane, kinetic diameter of 6.2 Å, and nil adsorption of $(C_4F_9)_3N$, kinetic diameter of 10 Å.

(b) Adsorption capacities of AlPO₄-5 (prepared in Example 2(b) supra) were measured using a standard McBain-Bakr gravimetric adsorption apparatus. The following data were obtained on a sample activated at 350° C.:

|             | Kinetic Diameter, Å | Pressure, Torr | Temp., °C | Wt. % Adsorbed |
|-------------|---------------------|----------------|-----------|----------------|
| $O_2$       | 3.46                | 99             | −183      | 13.3           |
| $O_2$       | 3.46                | 730            | −183      | 18.3           |
| Cyclohexane | 6.0                 | 54             | 24        | 9.5            |
| Neopentane  | 6.2                 | 102            | 24        | 4.8            |
| $H_2O$      | 2.65                | 4.6            | 24        | 3.9            |

-continued

| | Kinetic Diameter, Å | Pressure, Torr | Temp., °C | Wt. % Adsorbed |
|---|---|---|---|---|
| $H_2O$ | 2.65 | 21.0 | 24 | 29.8 |

The pore size of the calcined product is greater than 6.2 Å, as shown by adsorption of neopentane, kinetic diameter of 6.2 Å.

(c) Adsorption capacities of $AlPO_4$-5 (prepared in a manner similar to that of example 2(b) supra) were measured using a standard McBain-Bakr gravimetric adsorption apparatus. The following data were obtained on a sample activated at 350° C.:

| | Kinetic Diameter Å | Pressure, torr | Temp., °C | Wt. % Adsorbed |
|---|---|---|---|---|
| $O_2$ | 3.46 | 105 | −183 | 14.6 |
| $O_2$ | 3.46 | 705 | −183 | 21.3 |
| Neopentane | 6.2 | 103 | 25 | 6.5 |
| $H_2O$ | 2.65 | 4.6 | 25 | 6.5 |
| $H_2O$ | 2.65 | 20.7 | 25 | 32.6 |

EXAMPLE 56

Adsorption capacities of $AlPO_4$-28 (prepared in Example 53(b), supra) were measured using a standard McBain-Bakr gravimetric adsorption apparatus. The following data were obtained on a sample activated at 350° C.:

| | Kinetic Diameter, Å | Pressure, Torr | Temp., °C | Wt. % Adsorbed |
|---|---|---|---|---|
| $O_2$ | 3.46 | 103 | −183 | 1.0 |
| $O_{hd\ 2}$ | 3.46 | 761 | −183 | 2.5 |
| n-Hexane | 4.3 | 28 | 24 | 0.4 |
| Neopentane | 6.2 | 310 | 24 | 0.5 |
| $H_2O$ | 2.65 | 4.6 | 24 | 11.1 |
| $H_2O$ | 2.65 | 20.0 | 24 | 21.4 |

The pore size of the calcined product is >2.65 Å, and <3.46 Å, as shown by adsorption of $H_2O$, kinetic diameter of 2.65 Å, and nil adsorption of $O_2$, kinetic diameter of 3.46 Å.

EXAMPLE 57

Adsorption capacities of $AlPO_4$-25 (prepared in Ex. 52(c), supra) were measured using a standard McBain Bakr gravimetric adsorption apparatus. The following data were obtained on a sample activated at 350° C.:

| | Kinetic Diameter, Å | Pressure, Torr | Temp., °C | Wt. % Adsorbed |
|---|---|---|---|---|
| $O_2$ | 3.46 | 103 | −183 | 4.9 |
| $O_2$ | 3.46 | 761 | −183 | 5.9 |
| n-Hexane | 4.3 | 28 | 25 | 0.3 |
| Neopentane | 6.2 | 310 | 25 | 0.4 |
| $H_2O$ | 2.65 | 4.6 | 25 | 4.4 |
| $H_2O$ | 2.65 | 20.0 | 25 | 16.6 |

The pore size of the calcined product is >3.4 Å and <4.3 Å, as shown by adsorption of $O_2$, kinetic diameter of 3.46 Å, and nil adsorption of n-hexane, kinetic diameter of 4.3 Å.

EXAMPLE 58

Adsorption capacities of $AlPO_4$-20 (prepared as in Example 47(b) supra) were measured using a standard McBain-Bakr gravimetric adsorption apparatus. The following data were obtained on a sample activated at 350° C.:

| | Kinetic Diameter, Å | Pressure Torr | Temp., °C | Wt. % Adsorbed |
|---|---|---|---|---|
| $O_2$ | 3.46 | 97 | −183 | 2.7 |
| $O_2$ | 3.46 | 750 | −183 | 11.5 |
| n-Hexane | 4.3 | 45 | 24 | 1.7 |
| neopentane | 6.2 | 303 | 24 | 1.5 |
| Cyclohexane | 6.0 | 11 | 24 | 1.3 |
| $H_2O$ | 2.65 | 4.6 | 24 | 22.6 |
| $H_2O$ | 2.65 | 18.5 | 24 | 37.2 |

The pore size of the calcined product is ca. 3 Å, as shown by adsorption of $H_2O$, kinetic diameter of 2.65 Å, and low adsorption at low partial pressures of $O_2$, kinetic diameter of 3.46 Å.

EXAMPLE 59

Adsorption capacities of $AlPO_4$-17 (prepared in Ex. 42(c) supra) using a standard McBain-Bakr gravimetric adsorption apparatus. The following data were obtained on a sample activated at 350° C.:

| | Kinetic Diameter, Å | Pressure Torr | Temp.,°C | Wt. % Adsorbed |
|---|---|---|---|---|
| $O_2$ | 3.46 | 102 | −183 | 22.2 |
| $O_2$ | 3.46 | 724 | −183 | 23.1 |
| n-Hexane | 4.3 | 45 | 23 | 7.7 |
| Isobutane | 5.0 | 101 | 22 | 0.2 |
| Neopentane | 6.2 | 308 | 23 | 0.3 |
| $H_2O$ | 2.65 | 4.6 | 22 | 24.9 |
| $H_2O$ | 2.65 | 18 | 22 | 27.8 |

The pore size of the calcined product is >4.3 Å and <5.0 Å, as shown by adsorption of n-hexane, kinetic diameter of 4.3 Å, and nil adsorption of isobutane, kinetic diameter of 5.0 Å.

EXAMPLE 60

Adsorption capacities of $AlPO_4$-16 (prepared in Example 41(d) supra) were measured using a standard McBain-Bakr gravimetric adsorption apparatus. The following data were obtained on a sample activated at 350° C.:

| | Kinetic Diameter, Å | Pressure Torr | Temp., °C | Adsorbed |
|---|---|---|---|---|
| $O_2$ | 3.46 | 101 | −183 | 1.2 |
| $O_2$ | 3.46 | 755 | −183 | 11.6 |
| n-Butane | 4.3 | 768 | 24 | 2.0 |
| Neopentane | 6.2 | 301 | 25 | 1.4 |
| $H_2O$ | 2.65 | 4.6 | 24 | 19.0 |
| $H_2O$ | 2.65 | 20 | 24 | 36.3 |

The pore size of the calcined product is >2.65 and <3.46 Å, as shown by adsorption of $H_2O$, kinetic diameter of 2.65 Å, and low absorption of $O_2$ at low partial pressures, kinetic diameter of 3.46 Å.

EXAMPLE 61

Adsorption capacities of $AlPO_4$-14 (prepared in Ex. 39(b) supra) using a standard McBain-Bakr gravimetric adsorption apparatus. The following data were obtained on a sample activated at 350° C.:

| Adsorbate | Kinetic Diameter, Å | Pressure, Torr | Temp., °C | Wt. % Adsorbed |
|---|---|---|---|---|
| $O_2$ | 3.46 | 102 | −183 | 15.53 |
| $O_2$ | 3.46 | 763 | −183 | 21.56 |
| n-Hexane | 4.3 | 45 | 26 | 0.25 |
| neopentane | 6.2 | 499 | 24 | 0.37 |
| $H_2O$ | 2.65 | 4.6 | 24 | 21.46 |
| $H_2O$ | 2.65 | 21.0 | 24 | 28.66 |
| $N_2$ | 3.64 | 100 | −196 | 11.28 |
| $N_2$ | 3.64 | 747 | −196 | 14.99 |

The pore size of the calcined product is >3.64 Å and <4.3 Å as shown by adsorption of $N_2$, kinetic diameter of 3.64 Å, and nil adsorption of n-hexane, kinetic diameter of 4.3 Å.

EXAMPLE 62-A

Adsorption capacities of $AlPO_4$-8 (prepared as in Example 29, supra) using a standard McBain-Bakr gravimetric adsorption apparatus. The following data were obtained on a sample activated at 350° C.:

| | Kinetic Diameter, Å | Pressure Torr | Temp., °C | Wt. % Adsorbed |
|---|---|---|---|---|
| $O_2$ | 3.46 | 101 | −183 | 8.9 |
| $O_2$ | 3.46 | 755 | −183 | 18.6 |
| n-Butane | 4.3 | 768 | 24 | 5.0 |
| Neopentane | 6.2 | 501 | 24 | 4.5 |
| $(C_4F_9)_3N$ (After 4 hours) | 10 | 0.073 | 25 | 8.2 |
| $H_2O$ | 2.65 | 4.6 | 24 | 18.5 |
| $H_2O$ | 2.65 | 20.0 | 24 | 31.9 |

The pore size of the calcined product is greater than 6.2 Å, as shown by adsorption of neopentane, kinetic diameter of 6.2 Å.

EXAMPLE 62-B

Adsorption capacities of $AlPO_4$-31 (prepared as in Example 54(b) supra except that product was calcined to a temperature of 600° C.) were measured using a standard McBain-Bakr gravimetric adsorption apparatus. The following data were obtained on a sample activated at 350° C.:

| | Kinetic Diameter, Å | Pressure, Torr | Temp., °C | Wt. % Adsorbed |
|---|---|---|---|---|
| $O_2$ | 3.46 | 99 | −183 | 8.1 |
| $O_2$ | 3.46 | 711 | −183 | 11.5 |
| Butane | 4.3 | 107 | 24 | 4.0 |
| Cyclohexane | 6.0 | 54 | 24 | 5.3 |
| Neopentane | 6.2 | 109 | 24 | 3.1 |
| $H_2O$ | 2.65 | 4.6 | 24 | 5.3 |
| $H_2O$ | 2.65 | 14.0 | 24 | 13.9 |

The pore size is larger than 6.2 Å as shown by the adsorption of neopentane.

EXAMPLE 63

A portion of the crystalline $AlPO_4$-11 product of Example 32(a) supra was calcined in air from 200° C. to 500° C. over a period of 1 hour, followed by heating at 500° C. for 2 hours.

Adsorption capacities were measured on this calcined product using a standard McBain-Bakr gravimetric adsorption apparatus. The following data were obtained on a sample activated at 350° C.:

| Adsorbate | Kinetic Diameter, Å | Pressure Torr | Temp., °C | Wt. % Adsorbed |
|---|---|---|---|---|
| $O_2$ | 3.46 | 101 | −183 | 9.22 |
| $O_2$ | 3.46 | 755 | −183 | 10.7 |
| N-butane | 4.3 | 304 | 24 | 4.35 |
| Isobutane | 5.0 | 502 | 24 | 4.71 |
| Neopentane | 6.2 | 301 | 24 | 1.22 |
| Cyclohexane | 6.0 | 30 | 24 | 5.30 |
| $H_2O$ | 2.65 | 4.6 | 24 | 11.8 |
| $H_2O$ | 2.65 | 20.0 | 24 | 16.4 |

The pore size of the calcined product is greater than 6.0 Å and less than 6.2 Å, as shown by adsorption of cyclohexane, kinetic diameter of 6.0 Å, and nil adsorption of neopentane, kinetic diameter of 6.2 Å.

EXAMPLE 64

Adsorption capacities of $AlPO_4$-18 (prepared in Example 46(b) supra) were measured using a standard McBain-Bakr gravimetric adsorption apparatus. The following data were obtained on a sample activated at 350° C.:

| | Kinetic Diameter, Å | Pressure, torr | Temp. °C. | Wt. % Adsorbed |
|---|---|---|---|---|
| $O_2$ | 3.46 | 130 | −183 | 23.0 |
| $O_2$ | 3.46 | 697 | −183 | 27.9 |
| n-Butane | 4.3 | 718 | 24 | 16.2 |
| iso-Butane | 5.0 | 101 | 24 | 0.1 |
| $H_2O$/ | 2.65 | 4.6 | 24 | 30.3 |
| $H_2O$ | 2.65 | 21.0 | 24 | 36.9 |

The pore size of the calcined product is 4.3 and 5.0 Å, as shown by adsorption of n-butane and nil adsorption of iso-butane at low partial pressure.

Somewhat surprisingly the aluminophosphate compositions of the present invention are found to be strongly hydrophilic. All species are observed to adsorb water preferentially over common hydrocarbon molecules such as paraffins, olefins and benzenoid aromatic species, e.g., benzene, xylenes and cumene. Thus the present invention aluminophosphates as a class are useful as desiccants in such adsorption separation/purification processes as natural gas drying, cracked gas drying. Water is also preferentially adsorbed over the so-called permanent gases such as carbon dioxide, nitrogen, oxygen and hydrogen. These aluminophosphates are therefore suitably employed in the drying of reformer hydrogen streams and in the drying of oxygen, nitrogen or air prior to liquefaction. In this respect the adsorptive properties of the present aluminophosphates appears to be quite similar to those of the low silica aluminosilicate zeolites, despite the fact that they exhibit essentially no ion-exchange capacity—a quintessential property of zeolites.

The adsorptive properties of the present $AlPO_4$-n compositions are illustrated by the data set forth in Table F and Table G below.

TABLE F

Static Drying of Moist Air at Room Temperature

| Sample | % Humidity Initial | % Humidity Final | Contact Time hours |
|---|---|---|---|
| Zeolite 4A | 60 | 21 | 3 |
| Zeolite 5A | 54 | 5 | 16 |
| Silica Gel | 56 | 18 | 16 |
| $AlPO_4$—5 | 55 | 29 | 4 |
| $AlPO_4$—8 | 60 | 21 | 3.5 |

TABLE F-continued

Static Drying of Moist Air at Room Temperature

| Sample | % Humidity Initial | % Humidity Final | Contact Time hours |
|---|---|---|---|
| " | 61 | 19 | 18 |
| AlPO₄—11 | 57 | 29 | 5.5 |
| AlPO₃—14 | 56 | 19 | 3.0 |
| AlPO₄—16 | 70 | 22 | 3.0 |
| " | 56 | 14 | 72 |
| AlPO₄—17 | 63 | 24 | 18.5 |
| AlPO₄—20 | 60 | 17 | 16 |
| AlPO₄—28 | 56 | 7 | 17.5 |
| AlPO₄—25 | 56 | 25 | 18.5 |
| AlPO₄—9 | 51 | 29 | 23 |
| AlPO₄—18 | 56 | 19 | 24 |
| AlPO₄—31 | 51 | 24 | 19 |

To illustrate the hydrophilic character of the AlPO₄-n compositions in contact with an aqueous organic solution, dehydrated samples of AlPO₄ compounds and prior known comparison adsorbent, each weighing 0.5 grams were placed in 2 grams of a solution of 4 vol.-% H₂O and 96 vol.-% 2-butanone at ambient room temperature and agitated moderately for 2 hours. Thereafter the residual solution and the adsorbent were analyzed for water content. The results appear below:

TABLE G

| Adsorbent | % Water Removal from Solution | % Loading** |
|---|---|---|
| AlPO₄—5 | 55 | 23 |
| AlPO₄—8 | 74 | 45 |
| AlPO₄—11 | 21 | 23 |
| AlPO₄—14 | >80 | >45 |
| AlPO₄—16 | >80 | >45 |
| AlPO₄—17 | 77 | 41 |
| AlPO₄—20 | 87 | 58 |
| Zeolite NaY | 80 | 37 |
| Silica Gel | 28 | — |
| Silicalite* | −5 | — |

*U.S. Pat. No. 4,061,724
**Percent of maximum theoretical capacity

The present AlPO₄-n compositions exhibit novel surface selectivity characteristics which render them useful as catalyst or catalyst bases in a number of hydrocarbon conversion and oxidative combustion reactions. They can be impregnated or otherwise loaded with catalytically active metals by methods well known in the art and used, for example, in fabricating catalysts compositions having silicalite or alumina bases. Of the general class, those species having pores larger than about 5 Å are preferred.

Among the hydrocarbon conversion reactions catalyzed by AlPO₄-n compositions are cracking, hydrocracking, alkylation of both the aromatic and isoparaffin types, isomerization including xylene isomerization, polymerization, reforming, hydrogenation, dehydrogenation, transalkylation, dealkylation and hydration.

Using a AlPO₄-n catalysts compositions which contain a hydrogenation promoter such as platinum or palladium, heavy petroleum residual stocks, cyclic stocks and other hydrocrackable charge stocks can be hydrocracked at temperatures in the range of 400° F. to 825° F. using molar ratios of hydrogen to hydrocarbon in the range of between 2 and 80, pressures between 10 and 3500 p.s.i.g., and a liquid hourly space velocity (LHSV) of from 0.1 to 20, preferably 1.0 to 10.

The AlPO₄-n catalyst compositions employed in hydrocracking are also suitable for use in reforming processes in which the hydrocarbon feedstocks contact the catalyst at temperatures of from about 700° F. to 1000° F., hydrogen pressures of from 100 to 500 p.s.i.g., LHSV values in the range of 0.1 to 10 and hydrogen to hydrocarbon molar ratios in the range of 1 to 20, preferably between 4 and 12.

These same catalysts, i.e. those containing hydrogenation promoters, are also useful in hydroisomerization processes in which feedstocks such as normal paraffins are converted to saturated branched chain isomers. Hydroisomerization is carried out at a temperature of from about 200° F. to 600° F., preferably 300° F. to 550° F. with an LHSV value of from about 0.2 to 1.0. Hydrogen is supplied to the reactor in admixture with the hydrocarbon feedstock in molar proportions (H/Hc) of between 1 and 5.

At somewhat higher temperatures, i.e. from about 650° F. to 1000° F., preferably 850° F. to 950° F. and usually at somewhat lower pressures within the range of about 15 to 50 p.s.i.g., the same catalyst compositions are used to hydroisomerize normal paraffins. Preferably the paraffin feedstock comprises normal paraffins having a carbon number range of C₇–C₂₀. Contact time between the feedstock and the catalyst is generally relatively short to avoid undesireable side reactions such as olefin polymerization and paraffin cracking. LHSV values in the range of 0.1 to 10, preferably 1.0 to 6.0 are suitable.

The unique crystal structure of the present AlPO₄ catalysts and their total lack of alkali metal content favor their use in the conversion of alkylaromatic compounds, particularly the catalytic disproportionation of toluene, ethylene, trimethyl benzenes, tetramethyl benzenes and the like. In the disproportionation process isomerization and transalkylation can also occur. Group VIII noble metal adjuvants alone or in conjunction with Group VI-B metals such as tungsten, molybdenum and chromium are preferably included in the catalyst composition in amounts of from about 3 to 15 weight-% of the overall composition. Extraneous hydrogen can, but need not be present in the reaction zone which is maintained at a temperature of from about 400° to 750° F., pressures in the range of 100 to 2000 p.s.i.g. and LHSV values in the range of 0.1 to 15.

Catalytic cracking processes are preferably carried out with AlPO₄-n compositions using feedstocks such as gas oils, heavy naphthas, deasphalted crude oil residua etc. with gasoline being the principal desired product. Temperature conditions of 850° to 1100° F., LHSV values of 0.5 to 10 and pressure conditions of from about 0 to 50 p.s.i.g. are suitable.

Dehydrocyclization reactions employing paraffinic hydrocarbon feedstocks, preferably normal paraffins having more than 6 carbon atoms, to form benzene, xylenes, toluene and the like are carried out using essentially the same reaction conditions as for catalytic cracking. For these reactions it is preferred to use the AlPO₄-n catalyst in conjunction with a Group VIII non-noble metal cation such as cobalt and nickel.

In catalytic dealkylation wherein it is desired to cleave paraffinic side chains from aromatic nuclei without substantially hydrogenating the ring structure, relatively high temperatures in the range of about 800°–1000° F. are employed at moderate hydrogen pressures of about 300–1000 p.s.i.g., other conditions being similar to those described above for catalytic hydrocracking. Preferred catalysts are of the same type described above in connection with catalytic dehydrocyclization. Particularly desirable dealkylation reactions contemplated herein include the conversion of methylnaphthalene to naphthalene and toluene and/or xylenes to benzene.

In catalytic hydrofining, the primary objective is to promote the selective hydrodecomposition of organic sulfur and/or nitrogen compounds in the feed, without substantially affecting hydrocarbon molecules therein. For this purpose it is preferred to employ the same general conditions described above for catalytic hydrocracking, and catalysts of the same general nature described in connection with dehydrocyclization operations. Feedstocks include gasoline fractions, kerosenes, jet fuel fractions, diesel fractions, light and heavy gas oils, deasphalted crude oil residua and the like any of which may contain up to about 5 weight-percent of sulfur and up to about 3 weight-percent of nitrogen.

Similar conditions can be employed to effect hydrofining, i.e., denitrogenation and desulfurization, of hydrocarbon feeds containing substantial proportions of organonitrogen and organosulfur compounds. It is generally recognized that the presence of substantial amounts of such constituents markedly inhibits the activity of catalysts for hydrocracking. Consequently, it is necessary to operate at more extreme conditions when it is desired to obtain the same degree of hydrocracking conversion per pass on a relatively nitrogenous feed than are required with a feed containing less organonitrogen compounds. Consequently, the conditions under which denitrogenation, desulfurization and/or hydrocracking can be most expeditiously accomplished in any given situation are necessarily determined in view of the characteristics of the feedstocks in particular the concentration of organonitrogen compounds in the feedstock. As a result of the effect of organonitrogen compounds on the hydrocracking activity of these compositions it is not at all unlikely that the conditions most suitable for denitrogenation of a given feedstock having a relatively high organonitrogen content with minimal hydrocracking, e.g., less than 20 volume percent of fresh feed per pass, might be the same as those preferred for hydrocracking another feedstock having a lower concentration of hydrocracking inhibiting constituents e.g., organonitrogen compounds. Consequently, it has become the practice in this art to establish the conditions under which a certain feed is to be contacted on the basis of preliminary screening tests with the specific catalyst and feedstock.

Isomerization reactions are carried out under conditions similar to those described above for reforming, using somewhat more acidic catalysts. Olefins are preferably isomerized at temperatures of 500°–900° F., while paraffins, naphthenes and alkyl aromatics are isomerized at temperatures of 700°–1000° F. Particularly desirable isomerization reactions contemplated herein include the conversion of n-heptane and/or n-octane to isoheptanes, iso-octanes, butane and isobutane, methylcyclopentane to cyclohexane, metaxylene and/or ortho-xylene to paraxylene, 1-butene to 2-butene and/or isobutene, n-hexene to iso-hexene, cyclohexene to methylcyclopentene etc. The preferred cation form is a combination of the AlPO$_4$-n with polyvalent metal compounds (such as sulfides) of metals of Group II-A, Group II-B and rare earth metals. For alkylation and dealkylation processes the AlPO$_4$-n compositions having pores of at least 5 A are preferred. When employed for dealkylation of alkyl aromatics, the temperature is usually at least 350° F. and ranges up to a temperature at which substantial cracking of the feedstock or conversion products occurs, generally up to about 700° F. The temperature is preferably at least 450° F. and not greater than the critical temperature of the compound undergoing dealkylation. Pressure conditions are applied to retain at least the aromatic feed in the liquid state. For alkylation the temperature can be as low as 250° F. but is preferably at least 350° F. In alkylation benzene, toluene and xylene, the preferred alkylating agent are olefins such as ethylene and propylene.

What is claimed is:

1. Crystalline aluminophosphates each having a framework structure whose chemical composition expressed in terms of mole ratios of oxides is:

Al$_2$O$_3$:1.0±0.2 P$_2$O$_5$:

each of said framework structures being microporous in which the pores are uniform and have nominal diameters within the range of about 3 to about 10 Angstroms, an intracrystalline adsorption capacity for water at 4.6 torr and 24° C. of at least 3.5 weight percent, the adsorption and desorption of water being completely reversible while retaining the same essential framework topology in both the hydrated and dehydrated state.

2. Crystalline aluminophosphate according to claim 1 which has an X-ray powder diffraction pattern which contains at least the d-spacings set forth in Table 2.

3. Crystalline aluminophosphate according to claim 1 which has an X-ray powder diffraction pattern which contains at least the d-spacings set forth in Table 4.

4. Crystalline aluminophosphate according to claim 1 which has an X-ray powder diffraction pattern which contains at least the d-spacings set forth in Table 6.

5. Crystalline aluminophosphate according to claim 1 which has an X-ray powder diffraction pattern which contains at least the d-spacings set forth in Table 8.

6. Crystalline aluminophosphate according to claim 1 which has an X-ray powder diffraction pattern which contains at least the d-spacings set forth in Table 10.

7. Crystalline aluminophosphate according to claim 1 which has an X-ray powder diffraction pattern which contains at least the d-spacings set forth in Table 12.

8. Crystalline aluminophosphate according to claim 1 which has an X-ray powder diffraction pattern which contains at least the d-spacings set forth in Table 13.

9. Crystalline aluminophosphate according to claim 1 which has an X-ray powder diffraction pattern which contains at least the d-spacings set forth in Table 15.

10. Crystalline aluminphosphate according to claim 1 which has an X-ray powder diffraction pattern which contains at least the d-spacings set forth in Table 17.

11. Crystalline aluminophosphate according to claim 1 which has an X-ray powder diffraction pattern which contains at least the d-spacings set forth in Table 19.

12. Crystalline aluminophosphate according to claim 1 which has an X-ray powder diffraction pattern which contains at least the d-spacings set forth in Table 21.

13. Crystalline aluminophosphate according to claim 1 which has an X-ray powder diffraction pattern which contains at least the d-spacings set forth in Table 23.

14. Crystalline aluminophosphate according to claim 1 which has an X-ray powder diffraction pattern essentially as set forth in Table 24.

15. Crystalline aluminophosphate according to claim 1 which has an X-ray powder diffraction pattern which contains at least the d-spacings set forth in Table 25.

16. Crystalline aluminophosphate according to claim 1 which has an X-ray powder diffraction pattern essentially as set forth in Table 26.

17. Process for preparing a microporous crystalline aluminophosphate which comprises forming a reaction mixture having a composition expressed in terms of mole ratios of oxides of $Al_2O_3:1\pm0.5\ P_2O_5:7-100\ H_2O$ and containing from about 0.2 to 2.0 moles of an organic templating agent per mole of $Al_2O_3$, and heating said reaction mixture at a temperature of at least 100° C. under autogeneous pressure until crystals of said aluminophosphate are produced.

18. Process according to claim 17 wherein the reaction mixture is heated at a temperature of from 100° C. to 300° C. under autogeneous pressure.

19. Process according to claim 18 wherein the reaction mixture has a composition expressed in terms of mole ratios of oxides of $Al_2O_3:0.8-1.2\ P_2O_5:25-75\ H_2O$ and is heated at a temperature of from 125° C. to 200° C.

20. Process according to claim 19 wherein the source of $P_2O_5$ is phosphoric acid, the source of $Al_2O_3$ is pseudoboehmite hydrated aluminum oxide and the reaction mixture contains per mole of $Al_2O_3$, from 0.5 to 1.5 moles of organic templating agent, from 40 to 50 moles $H_2O$ and about 1.0 mole $P_2O_5$.

21. Process according to claim 19 wherein the templating agent is selected from the group consisting of tetrapropylammonium hydroxide; tetraethylammonium hydroxide; tripropylamine; triethylamine; triethanolamine; piperidine; cyclohexylamine; 2-methyl pyridine; N,N-dimethylbenzylamine, N,N-diethylethanolamine, dicyclohexylamine; N,N-dimehylethanolamine; choline; N,N-dimethylpiperazine; 1,4-diazabicyclo (2,2,2) octane; N-methyldiethanolamine; N-methylethanolamine; N-methylpiperidine; 3-methylpiperidine; N-methylcyclohexylamine; 3-methylpyridine; 4-methylpyridine; quinuclidine; and N,N'-dimethyl-1,4-diazabicyclo (2,2,2) octane dihydroxide.

22. Process according to claim 19 wherein the templating agent is selected from the group consisting of tetramethylammonium hydroxide; tetraethylammonium hydroxide; tetrabutylammonium hydroxide; tetrapentylammonium hydroxide; di-(n-butyl)-amine; neopentylamine; di-(n-pentyl)-amine; isopropylamine and t-butylamine.

23. Process according to claim 19 wherein the templating agent is an alkyl amine in which the alkyl moiety contains from 2 to 7 carbon atoms.

24. Process according to claim 19 wherein the templating agent is selected from the group consisting of ethylenediamine and 2-imidazolidone.

25. Process according to claim 23 wherein the alkylamine is di-(n-propyl) amine.

26. Process according to claims 19 wherein the templating agent is a polymeric quaternary ammonium salt $[(C_{14}H_{32}N_2)(OH)_2]_x$ wherein X is a value of at least 2.

* * * * *